United States Patent
Kostrzewski

(10) Patent No.: US 9,713,466 B2
(45) Date of Patent: Jul. 25, 2017

(54) ADAPTOR FOR SURGICAL INSTRUMENT FOR CONVERTING ROTARY INPUT TO LINEAR OUTPUT

(71) Applicant: Covidien LP, Mansfield, MA (US)

(72) Inventor: Stanislaw Kostrzewski, Newton, CT (US)

(73) Assignee: Covidien LP, Mansfield, MA (US)

( * ) Notice: Subject to any disclaimer, the term of this patent is extended or adjusted under 35 U.S.C. 154(b) by 571 days.

(21) Appl. No.: 14/279,928

(22) Filed: May 16, 2014

(65) Prior Publication Data
US 2015/0327850 A1 Nov. 19, 2015

(51) Int. Cl.
*A61B 17/04* (2006.01)
*F16H 25/18* (2006.01)
(Continued)

(52) U.S. Cl.
CPC ........ *A61B 17/0469* (2013.01); *A61B 17/072* (2013.01); *A61B 17/07207* (2013.01);
(Continued)

(58) Field of Classification Search
CPC . F16H 25/2018; F16H 25/186; A61B 17/072; A61B 17/115; A61B 2017/2903; A61B 2017/00398; A61B 2017/00464; A61B 2017/00473; A61B 2017/2915; A61B 2017/2916; A61B 2017/00371; A61B 17/0469; A61B 17/07207; Y10T 74/18312
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

CA 2451558 A1 1/2003
CN 101856251 A 10/2010
(Continued)

OTHER PUBLICATIONS

Extended European Search Report corresponding to International Application No. EP 15 15 1076.5 dated Apr. 22, 2015.
(Continued)

*Primary Examiner* — Richard Louis

(57) ABSTRACT

An adaptor for a powered surgical instrument includes a casing, a cam drum, a first linear driver, and a second linear driver. The cam drum defines and is translatable along a longitudinal axis of the adaptor between a retracted position and an advanced position. The cam drum is being supported for rotation about the longitudinal axis. The cam drum defines first and second radial cam grooves about an outer surface thereof. The first cam groove defines a first profile and the second cam groove defines a second profile. The first linear driver includes a first cam follower disposed in the first cam groove and the second linear driver includes a second cam follower disposed in the second cam groove. The first and second linear drivers are supported for movement between advanced and retracted positions in response to rotation of the cam drum.

20 Claims, 19 Drawing Sheets

(51) Int. Cl.
*F16H 25/20* (2006.01)
*A61B 17/072* (2006.01)
*A61B 17/115* (2006.01)
*A61B 17/00* (2006.01)
*A61B 17/29* (2006.01)

(52) U.S. Cl.
CPC .......... *A61B 17/115* (2013.01); *F16H 25/186* (2013.01); *F16H 25/2018* (2013.01); *A61B 2017/00371* (2013.01); *A61B 2017/00398* (2013.01); *A61B 2017/00464* (2013.01); *A61B 2017/00473* (2013.01); *A61B 2017/2903* (2013.01); *A61B 2017/2915* (2013.01); *A61B 2017/2916* (2013.01); *Y10T 74/18312* (2015.01)

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,312,023 A | 5/1994 | Green et al. | |
| 5,326,013 A | 7/1994 | Green et al. | |
| 5,350,355 A | 9/1994 | Sklar | |
| 5,374,275 A | 12/1994 | Bradley et al. | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,413,267 A | 5/1995 | Solyntjes et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,647,526 A | 7/1997 | Green et al. | |
| 5,653,374 A | 8/1997 | Young et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,779,130 A | 7/1998 | Alesi et al. | |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,865,361 A | 2/1999 | Milliman et al. | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,017,354 A | 1/2000 | Culp et al. | |
| 6,045,560 A | 4/2000 | McKean et al. | |
| 6,090,123 A | 7/2000 | Culp et al. | |
| 6,129,547 A | 10/2000 | Cise et al. | |
| 6,165,169 A | 12/2000 | Panescu et al. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,792,390 B1 | 9/2004 | Burnside et al. | |
| 6,817,508 B1 | 11/2004 | Racenet et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,899,538 B2 | 5/2005 | Matoba | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 7,032,798 B2 | 4/2006 | Whitman et al. | |
| 7,055,731 B2 | 6/2006 | Shelton, IV et al. | |
| 7,077,856 B2 | 7/2006 | Whitman | |
| 7,111,769 B2 | 9/2006 | Wales et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,246,734 B2 | 7/2007 | Shelton, IV | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,481,347 B2 | 1/2009 | Roy | |
| 7,487,899 B2 | 2/2009 | Shelton, IV et al. | |
| 7,549,564 B2 | 6/2009 | Boudreaux | |
| 7,568,603 B2 | 8/2009 | Shelton, IV et al. | |
| 7,575,144 B2 | 8/2009 | Ortiz et al. | |
| 7,588,175 B2 | 9/2009 | Timm et al. | |
| 7,588,176 B2 | 9/2009 | Timm et al. | |
| 7,637,409 B2 | 12/2009 | Marczyk | |
| 7,641,093 B2 | 1/2010 | Doll et al. | |
| 7,644,848 B2 | 1/2010 | Swayze et al. | |
| 7,670,334 B2 | 3/2010 | Hueil et al. | |
| 7,673,780 B2 | 3/2010 | Shelton, IV et al. | |
| 7,721,931 B2 | 5/2010 | Shelton, IV et al. | |
| 7,738,971 B2 | 6/2010 | Swayze et al. | |
| 7,740,159 B2 | 6/2010 | Shelton, IV et al. | |
| 7,743,960 B2 | 6/2010 | Whitman et al. | |
| 7,758,613 B2 | 7/2010 | Whitman | |
| 7,766,210 B2 | 8/2010 | Shelton, IV et al. | |
| 7,770,773 B2 | 8/2010 | Whitman et al. | |
| 7,770,775 B2 | 8/2010 | Shelton, IV et al. | |
| 7,799,039 B2 | 9/2010 | Shelton, IV et al. | |
| 7,802,712 B2 | 9/2010 | Milliman et al. | |
| 7,803,151 B2 | 9/2010 | Whitman | |
| 7,845,537 B2 | 12/2010 | Shelton, IV et al. | |

(56) References Cited

U.S. PATENT DOCUMENTS

| | | |
|---|---|---|
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,947,034 B2 | 5/2011 | Whitman |
| 7,951,071 B2 | 5/2011 | Whitman et al. |
| 7,963,433 B2 | 6/2011 | Whitman et al. |
| 7,967,178 B2 | 6/2011 | Scirica et al. |
| 7,992,758 B2 | 8/2011 | Whitman et al. |
| 8,016,855 B2 | 9/2011 | Whitman et al. |
| 8,020,743 B2 | 9/2011 | Shelton, IV |
| 8,035,487 B2 | 10/2011 | Malackowski |
| 8,056,787 B2 | 11/2011 | Boudreaux et al. |
| 8,114,118 B2 | 2/2012 | Knodel et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,220,367 B2 | 7/2012 | Hsu |
| 8,241,322 B2 | 8/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,348,855 B2 | 1/2013 | Hillely et al. |
| 8,357,144 B2 | 1/2013 | Whitman et al. |
| 8,365,972 B2 | 2/2013 | Aranyi et al. |
| 8,372,057 B2 | 2/2013 | Cude et al. |
| 8,391,957 B2 | 3/2013 | Carlson et al. |
| 8,517,241 B2 | 8/2013 | Nicholas et al. |
| 8,657,177 B2 | 2/2014 | Scirica et al. |
| 8,672,206 B2 | 3/2014 | Aranyi et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0165794 A1 | 9/2003 | Matoba |
| 2004/0111012 A1 | 6/2004 | Whitman |
| 2004/0193146 A1 | 9/2004 | Lee et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0282091 A1 | 12/2006 | Shelton et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0015645 A1* | 1/2011 | Liu .................. A61B 17/3468 606/109 |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0317525 A1* | 11/2013 | Wingardner, III ..... A61B 17/04 606/145 |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0207125 A1 | 7/2014 | Applegate et al. |
| 2014/0207185 A1 | 7/2014 | Goble et al. |

(56) References Cited

U.S. PATENT DOCUMENTS

| | | |
|---|---|---|
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 1690502 A1 | 8/2006 |
| EP | 1736112 A1 | 12/2006 |
| EP | 1759652 A2 | 3/2007 |
| EP | 1769754 A1 | 4/2007 |
| EP | 1 813 203 A2 | 8/2007 |
| EP | 1813199 A1 | 8/2007 |
| EP | 1813211 A2 | 8/2007 |
| EP | 1908412 A2 | 4/2008 |
| EP | 1917929 A1 | 5/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2133028 A2 | 12/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2329773 A1 | 6/2011 |
| EP | 2333509 A1 | 6/2011 |
| EP | 2377472 A1 | 10/2011 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| FR | 2861574 A1 | 5/2005 |
| KR | 20120022521 A | 3/2012 |
| WO | 8705122 A1 | 8/1987 |
| WO | 9727807 A1 | 8/1997 |
| WO | 00/72760 A1 | 12/2000 |
| WO | 00/72765 A1 | 12/2000 |
| WO | 03/000138 A2 | 1/2003 |
| WO | 03/026511 A1 | 4/2003 |
| WO | 03/077769 A1 | 9/2003 |
| WO | 2004/107989 A1 | 12/2004 |
| WO | 2006/042210 A2 | 4/2006 |
| WO | 2007/026354 A1 | 3/2007 |
| WO | 2008/131362 A2 | 10/2008 |
| WO | 2008/133956 A2 | 11/2008 |
| WO | 2009039506 A1 | 3/2009 |
| WO | 2007014355 A3 | 4/2009 |
| WO | 2009/132359 A2 | 10/2009 |
| WO | 2011/108840 A2 | 9/2011 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, mailed Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action con-esponding to International Application No. EP 14 15 2236.7 dated Aug. 11, 2015.
Extended European Search Report corresponding to International Application No. EP 15 18 4915.5 dated Jan. 5, 2016.
International Search Report corresponding to PCT/US2005/027266, completed May 30, 2008 and mailed Jun. 18, 2008; (2 pp.).
Extended European Search Report corresponding to EP 08 25 2703.7, completed Oct. 23, 2008 and mailed Oct. 31, 2008; (7 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).

(56) References Cited

OTHER PUBLICATIONS

Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805. 3, dated Nov. 4, 2013.
Extended European Search Report from Application No. EP 13171742.3 dated Jan. 3, 2014.
Extended European Search Report corresponding to Application No. EP 14152236.7 mailed May 12, 2014.
Partial European Search Report from Application No. EP 14159056.2 dated Jun. 18, 2014 (8 pp).
European Search Report dated Sep. 3, 2015, issued in European Application No. 15170195.
European Search Report dated Oct. 7, 2015, issued in European Application No. 15167797.
"Universal S 3B Stand", Sep. 13, 2006, XP05521369, http://www.ophthalworld.de/cosmoshop/pix/a/media/28072015/Zeiss S3 Floor Stand User Manual.pdf.

\* cited by examiner

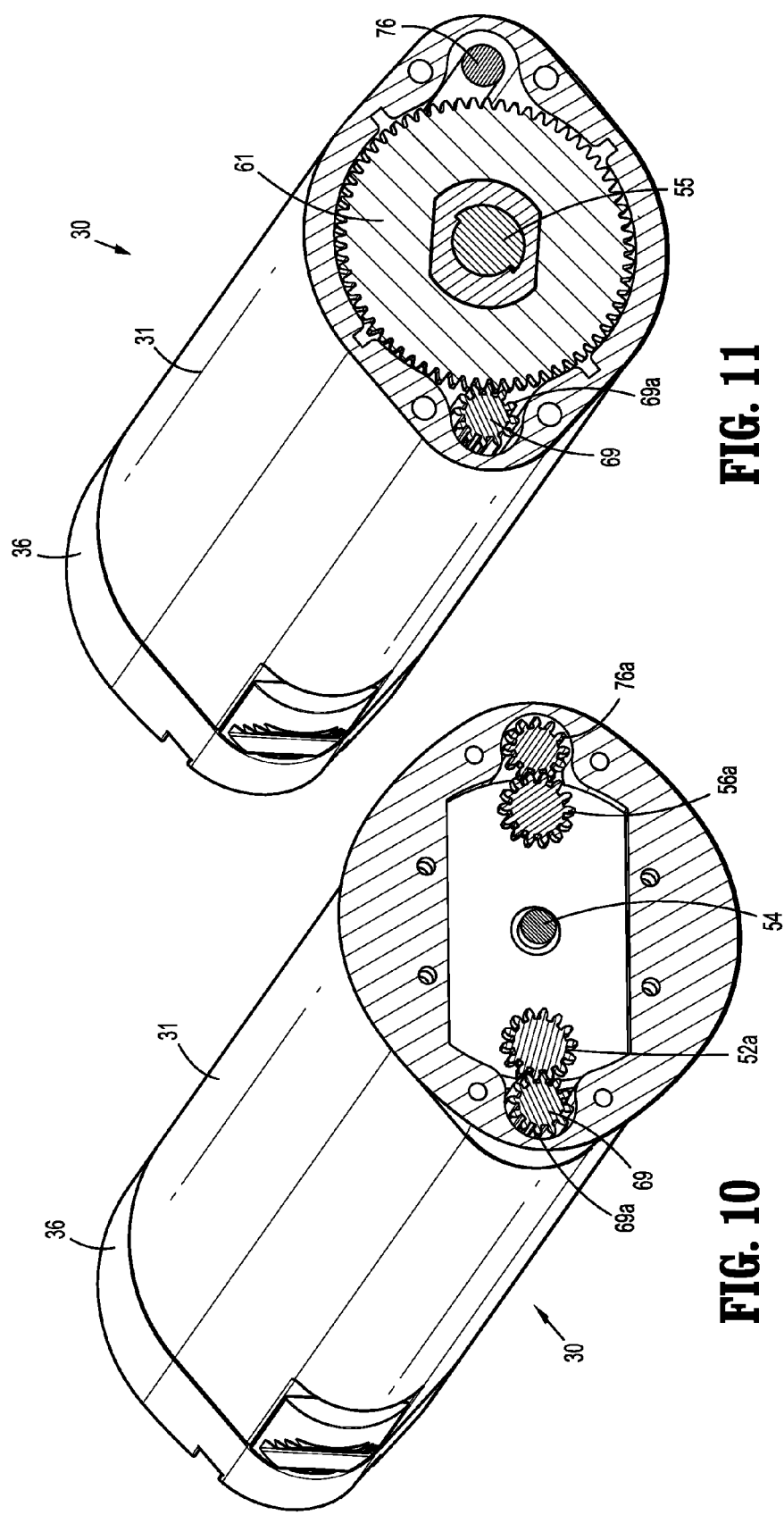

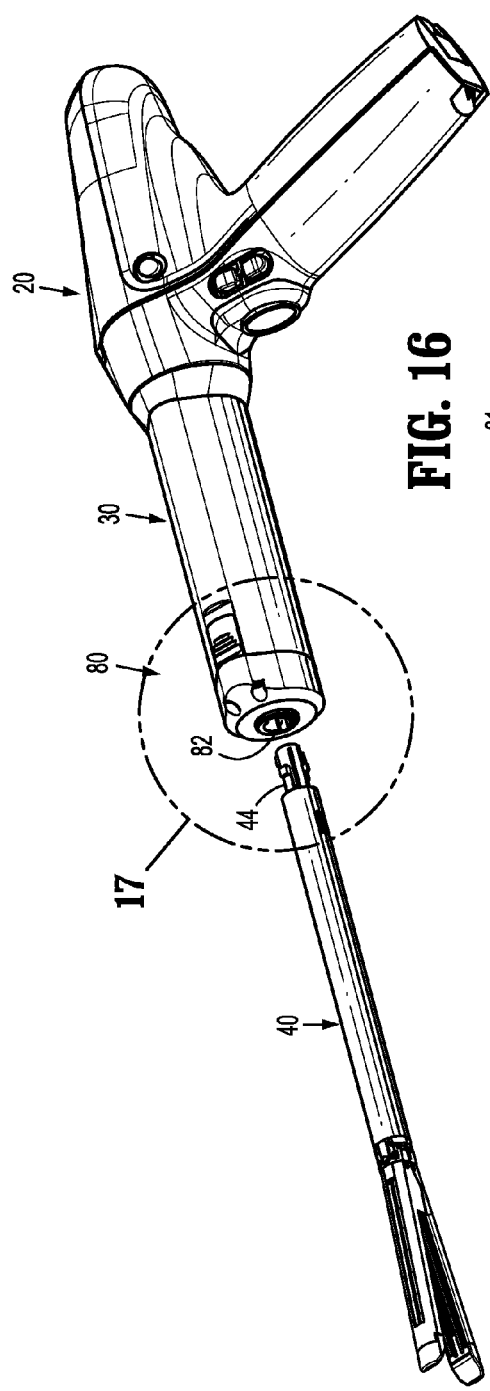
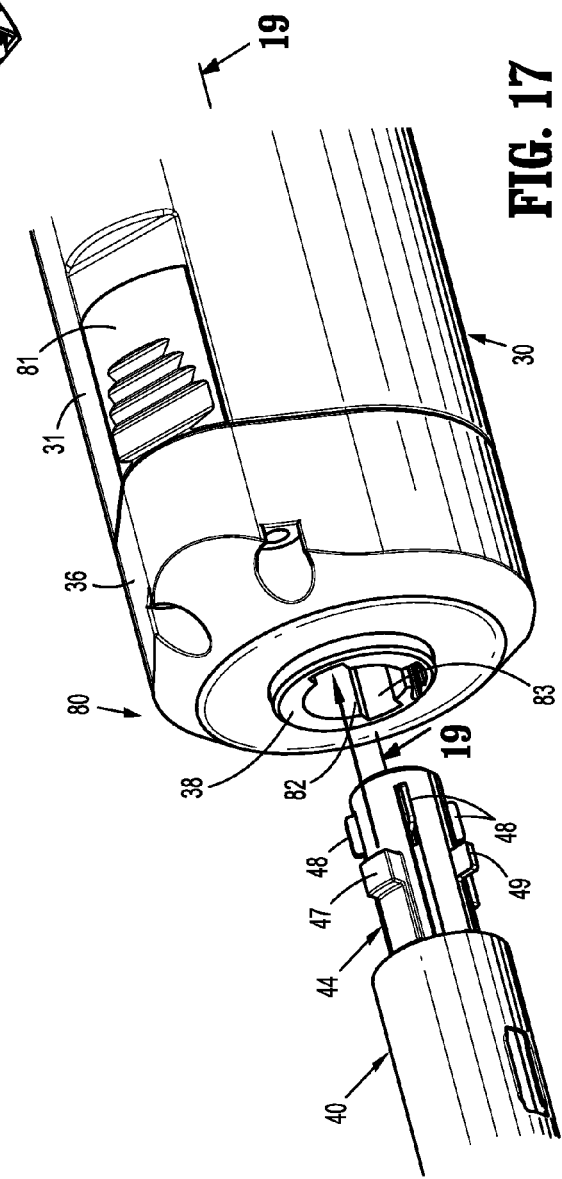
FIG. 16
FIG. 17

ADAPTOR FOR SURGICAL INSTRUMENT FOR CONVERTING ROTARY INPUT TO LINEAR OUTPUT

BACKGROUND

1. Technical Field

The present disclosure relates to surgical instruments and, more specifically, to an adaptor to convert rotary input from a handle of a surgical instrument into linear output for a loading unit.

2. Discussion of Related Art

As medical and hospital costs continue to increase, surgeons are constantly striving to develop advanced surgical techniques. Advances in the surgical field are often related to the development of operative techniques which involve less invasive surgical procedures which reduce overall patient trauma. In this manner, the length of hospital stays and thus, medical costs can be significantly reduced.

One of the truly great advances to reduce the invasiveness of surgical procedures is endoscopic surgery. Endoscopic surgery involves performing surgical procedures through small incisions formed in body walls. There are many common endoscopic surgical procedures, including arthroscopy, laparoscopy (pelviscopy), gastroentroscopy and laryngobronchoscopy, just to name a few. Typically, trocars are utilized for creating incisions through which the endoscopic surgery is performed. Trocar tubes or cannula devices can be extended through the incisions to provide access for endoscopic surgical tools. A camera or endoscope can be inserted through a trocar tube to permit visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, it is often necessary to suture body organs or tissue. Traditionally, suturing was accomplished by hand using a needle attached to a suture material. This procedure required open access to the tissue to be sutured. Upon the advent of endoscopic surgical procedures, endoscopic suturing instruments have been developed. The development of endoscopic suturing instruments is especially challenging because of the small openings through which the suturing of body organs or tissues must be accomplished.

A number of surgical device manufacturers have developed product lines with proprietary powered drive systems for operating and/or manipulating surgical devices. In many instances the surgical devices include a powered handle assembly, which is reusable, and a disposable loading unit or the like that is selectively connected to the powered handle assembly prior to use and then disconnected from the loading unit following use in order to be disposed of or in some instances sterilized for re-use.

Loading units for performing suturing procedures, endogastrointestinal anastomosis procedures, end-to-end anastomosis procedures, and transverse anastomosis procedures, typically require a linearly driven actuator to actuate the loading unit. As such, these loading units are not compatible with surgical devices and/or handle assemblies that have a rotary driven actuator.

In order to make linearly driven loading units compatible with powered surgical devices or handle assemblies that provide a rotary driven actuator, a need exists for adapters or adapter assemblies to interface between and interconnect the linearly driven loading units with the powered rotary driven surgical devices or handle assemblies.

SUMMARY

In an aspect of the present disclosure, an adaptor for a powered surgical instrument includes a casing, a cam drum, a first linear driver, and a second linear driver. The cam drum defines a longitudinal axis and is translatable between retracted and advanced positions in relation to the casing. The cam drum is supported for rotation about the longitudinal axis and defines first and second radial cam grooves about an outer surface thereof. The first cam groove defines a first profile and the second cam groove defines a second profile. The first linear driver includes a first cam follower disposed in the first cam groove. The first linear driver is supported for movement between advanced and retracted positions in relation to the cam drum along an axis parallel to the longitudinal axis in response to rotation of the cam drum about the longitudinal axis. The second linear driver includes a second cam follower disposed in the second cam groove. The second linear driver is supported for movement between advanced and retracted positions in relation to the cam drum along an axis parallel to the longitudinal axis in response to rotation of the cam drum about the longitudinal axis.

In aspects, the adaptor includes a lead screw that is rotatable about the longitudinal axis. The lead screw may be received within a lead screw passage defined by cam drum. Rotation of the cam drum may effect longitudinal translation of the cam drum and the first and second linear drivers along the longitudinal axis.

In some aspects, the second cam groove is positioned distal to the first cam groove.

In certain aspects, the adaptor includes a cam drum gear that is coupled to the cam drum. Rotation of the cam drum gear may effect rotation of the cam drum. In embodiments, the adaptor includes a middle gear and a cam drum input shaft disposed about axes that are parallel to the longitudinal axis. The cam drum input shaft may be engaged with the middle gear and the middle gear may be engaged with the cam drum gear such that rotation of the cam drum input shaft effects rotation of the cam drum. The middle gear may be in continuous engagement with the cam drum input shaft and the cam drum gear as the cam drum is longitudinally translated between the retracted and advanced positions.

In particular aspects, the first and second linear drivers define a first pair of linear drivers. In addition, as the cam drum is rotated, the first and second profiles of the first and second cam grooves translate the first pair of linear drivers through a cycle having four phases of movement. In the first phase of movement, the first and second linear drivers may longitudinally advance in relation to the casing. In the second phase of movement, the first linear driver may be longitudinally fixed in relation to the casing and the second linear driver may longitudinally advance in relation to the casing. In a third phase of movement, the first linear driver may be longitudinally fixed and the second linear driver may longitudinally retract in relation to the casing. In a fourth phase of movement, the first and second linear drivers may both be longitudinally fixed in relation to the casing.

In aspects, the adaptor includes a second pair of linear drivers having a third linear driver and a fourth linear driver. The third linear driver may include a third cam follower disposed in the first cam groove. The third linear driver may be supported for movement between advanced and retracted positions in relation to the cam drum along an axis parallel to the longitudinal axis in response to rotation of the cam drum about the longitudinal axis. The fourth linear driver may include a fourth cam follower disposed in the second cam groove. The fourth linear driver may be supported for movement between advanced and retracted positions in relation to the cam drum along an axis parallel to the longitudinal axis in response to rotation of the cam drum about the longitudinal axis. As the cam drum is rotated, the first and second profiles of the first and second cam grooves may translate the second pair of linear drivers through the cycle. The third linear driver may be positioned about the cam drum in opposed relation to the first linear driver and the fourth linear driver may be positioned about the cam drum in opposed relation to the second linear driver. In embodiments, the first, second, third, and fourth cam followers are positioned in the first and second cam grooves such that when the first pair of linear drivers begin the first phase of movement, the second pair of linear drivers is in the fourth phase of movement. In other embodiments, the first, second, third, and fourth cam followers are positioned in the first and second cam grooves such that when the first pair of linear drivers begin the third phase of movement, the second pair of linear drivers begin the first phase of movement.

In some aspects, the adaptor includes an articulation assembly having an articulation shaft, an articulation drum, an articulation cam, and an articulation arm. The articulation shaft may extend along an axis parallel to the longitudinal axis and may be engaged with the articulation drum to effect rotation of the articulation drum when the articulation shaft is rotated. The articulation cam may be disposed within the articulation drum. The articulation cam and the articulation drum may be radially fixed relative to one another. The articulation cam may define a proximal camming surface and the articulation drum may define a distal camming surface. The proximal and distal camming surfaces may be helical surfaces. The articulation arm may include an articulation cam follower that is disposed between the proximal and distal camming surfaces. The articulation cam follower may longitudinally translate between a first articulated position, a straight position, and a second articulated position as the articulation drum and the articulation cam are rotated about the longitudinal axis. The straight configuration of the articulation arm may be about halfway between the first and second articulated positions of the articulation arm.

In some aspects of the present disclosure, a powered surgical instrument includes a handle, an adaptor, and a loading unit. The handle includes a receiver. The adaptor may be any of the adaptors detailed herein and includes a casing, a handle interface, a cam drum, a first pair of linear drivers, a second pair of linear drivers, and a locking mechanism. The casing has proximal and distal end portions. The handle interface is disposed in the proximal end portion of the adaptor and is releasably coupled to the receiver of the handle. The locking mechanism is positioned adjacent the distal end portion of the casing. The locking mechanism includes a release switch and a lock bar that are operatively associated with one another. The locking mechanism has a locked configuration and an unlocked configuration. The loading unit includes a connector assembly that is releasably secured within the locking mechanism of the adaptor when the locking mechanism is in the locked configuration.

In aspects, the handle interface includes a cam drum input shaft that is operatively associated with the cam drum to rotate the cam drum about the longitudinal axis.

In some aspects, the adaptor includes a distal cover and an articulation assembly disposed substantially within the distal cover. The distal cover may be disposed over the distal end portion of the casing and may include an articulation shaft, an articulation drum, an articulation cam, and an articulation arm. The articulation shaft may extend along an axis parallel to the longitudinal axis and may be engaged with the articulation drum to effect rotation of the articulation drum when the articulation shaft is rotated. The articulation cam may be disposed within and radially fixed relative to the articulation drum. The articulation cam may define a proximal camming surface and the articulation drum may define a distal camming surface. The articulation arm may include an articulation cam follow that is positioned between the proximal and distal camming surfaces. As the articulation drum and the articulation cam are rotated about the longitudinal axis, the proximal and distal camming surfaces may engage the articulation cam follower to longitudinal translate the articulation arm between a first articulated position, a straight position, and a second articulated position. In embodiments, the locking mechanism includes a lock arm that is operatively associated with the lock bar and the articulation drum may define an articulation lock groove. When the articulation assembly is in the straight position, the articulation interlock groove may be aligned with the lock arm to receive the lock arm. When the articulation assembly is in an articulated position, the articulation interlock groove may be offset from the lock arm to prevent the locking mechanism from transitioning to the unlocked configuration.

In particular aspects, the distal end portion of the casing defines a locking opening and a locking groove and the loading unit includes a guide lug. The locking groove receiving the guide lug to align the loading unit with the adaptor. The distal end portion of the casing may define a lug lock in communication with the locking groove and radially offset from the locking groove. When the guide lug is captured in the lug lock, the loading unit may be secured to the adaptor. The lock bar may be disposed within the locking groove. In the locked configuration of the locking mechanism, the lock bar may extend past the lug lock to capture the guide lug in the lug lock. In the unlocked configuration of the locking mechanism, the lock bar may be retracted to a position proximal to the lug lock to allow the guide lug to rotate out of the lug lock.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 10 is a cross-sectional view taken along section line 10-10 of FIG. 9;

FIG. 11 is a cross-sectional view taken along section line 11-11 of FIG. 9;

FIG. 16 is a perspective view of the surgical instrument of FIG. 1 with the stitching loading unit separated from the stitching adaptor;

FIG. 17 is an enlarged view of the indicated area of detail of FIG. 16;

DETAILED DESCRIPTION

Figure 1:
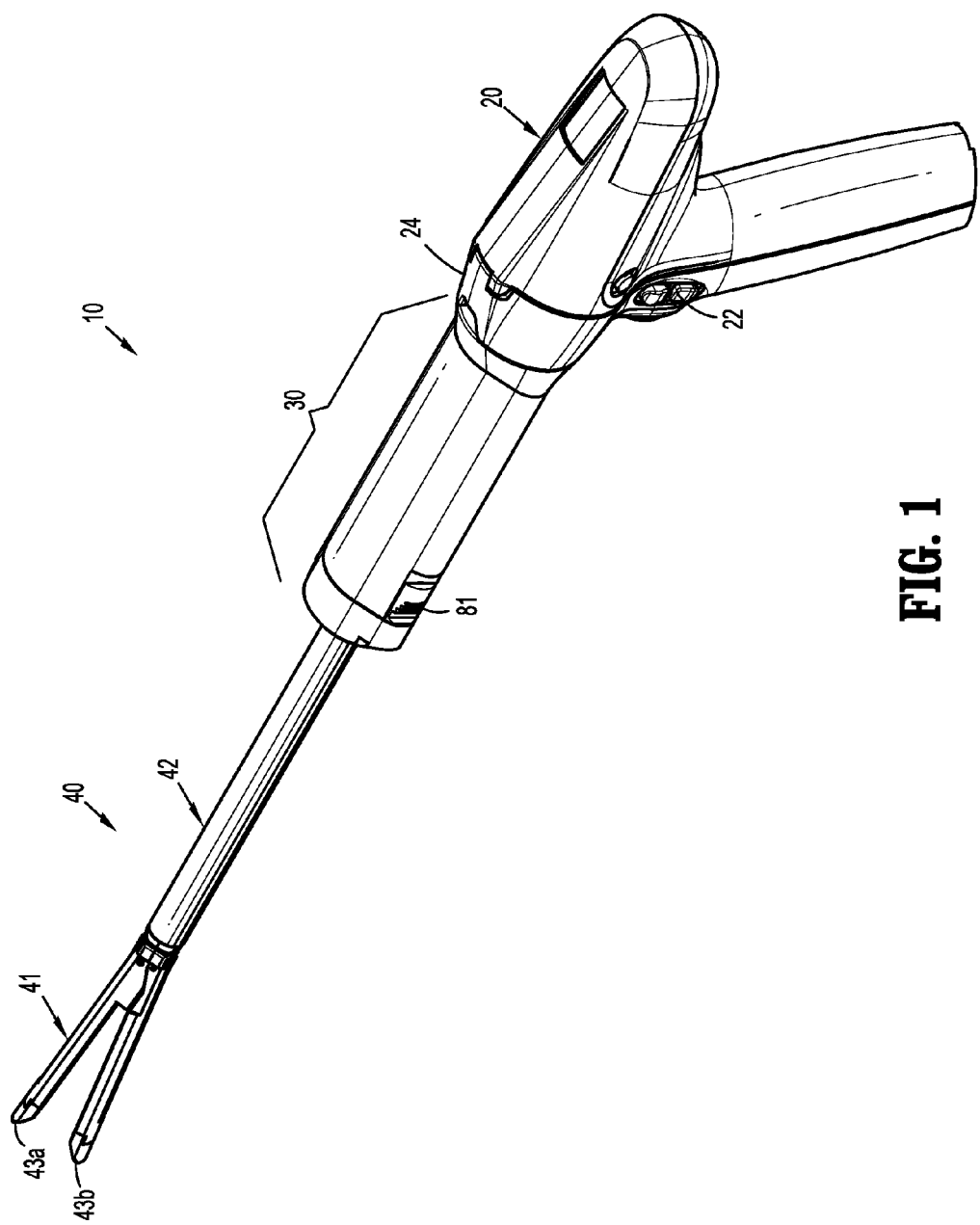
FIG. 1 is a rear perspective view of an embodiment of a surgical instrument in accordance with the present disclosure including a handle, a stitching adaptor, and a stitching loading unit.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is furthest from the clinician.

Figure 2:
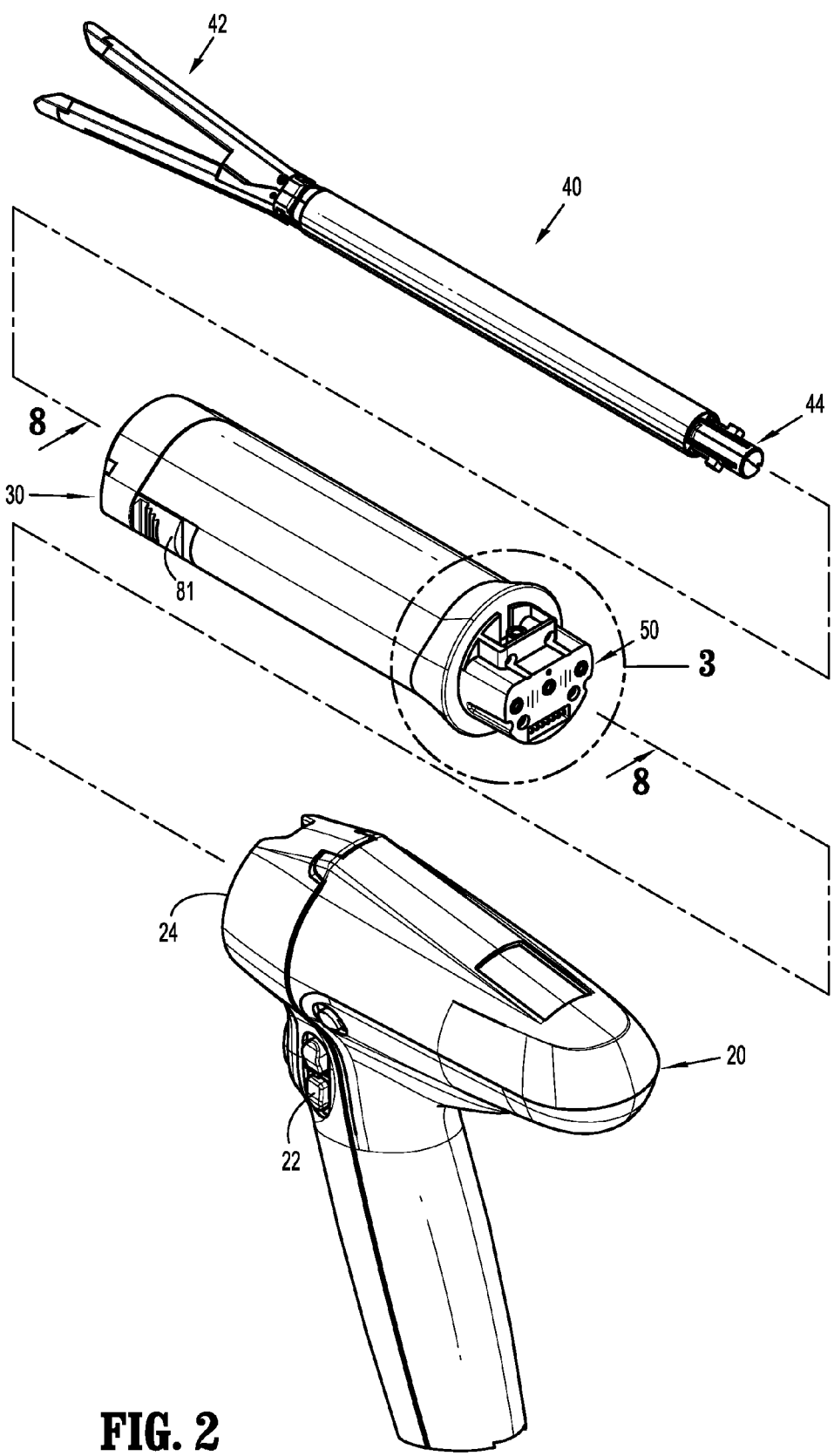
FIG. 2 is a rear perspective view of the surgical instrument of FIG. 1 with the parts separated.

Referring now to FIGS. 1 and 2, an exemplary embodiment of a surgical instrument 10 is provided in accordance with present disclosure including a handle 20, an adaptor 30, and a stitching loading unit 40. The surgical instrument 10 is configured to capture tissue within the stitching loading unit 40, create stitches through the captured tissue with sutures disposed within the stitching loading unit 40, and sever the captured tissue within the stitching loading unit 40. An exemplary embodiment of such a stitching loading unit is disclosed in commonly owned and co-pending U.S. patent application Ser. No. 14/507,900, the contents of which are hereby incorporated by reference in its entirety.

The handle 20 is a powered handle and may include one or more drive shafts (not shown) that rotate independently of one another. The handle 20 includes a control interface 22 and a receiver 24. The control interface 22 includes one or more control(s) associated with rotary drive shafts (not shown) within the handle 20 (e.g., an actuator button, a rotate button, a clamp button, a stitch button, etc.). The receiver 24 is supported at the distal end of the handle 20 and includes a recess configured to receive an interface (e.g., a handle interface 50 (FIG. 2) of the adaptor 30) of an adaptor or loading unit (e.g., a connector 44 of the loading unit 40). An exemplary example of such a powered handle is disclosed in commonly owned and co-pending U.S. patent application Ser. No. 13/484,975 filed May 31, 2012, and published as U.S. Patent Publication No. 2012/0253329 on Oct. 4, 2012, the contents of which are hereby incorporated by reference in its entirety. It is also contemplated that the handle 20 may be a manually driven handle with one or more output shafts.

The adaptor 30 converts the rotary motion of the drive shafts of the handle 20 into linear motion of linear drivers 65a-d (FIG. 5) to manipulate the stitching loading unit 40 as detailed below. The stitching loading unit 40 includes a jaw assembly 41 having first and second jaw members 43a, 43b for stitching and severing tissue captured therein, and a connector 44 (FIG. 2) for releasably securing the stitching loading unit 40 to the adaptor 30.

Figure 3:
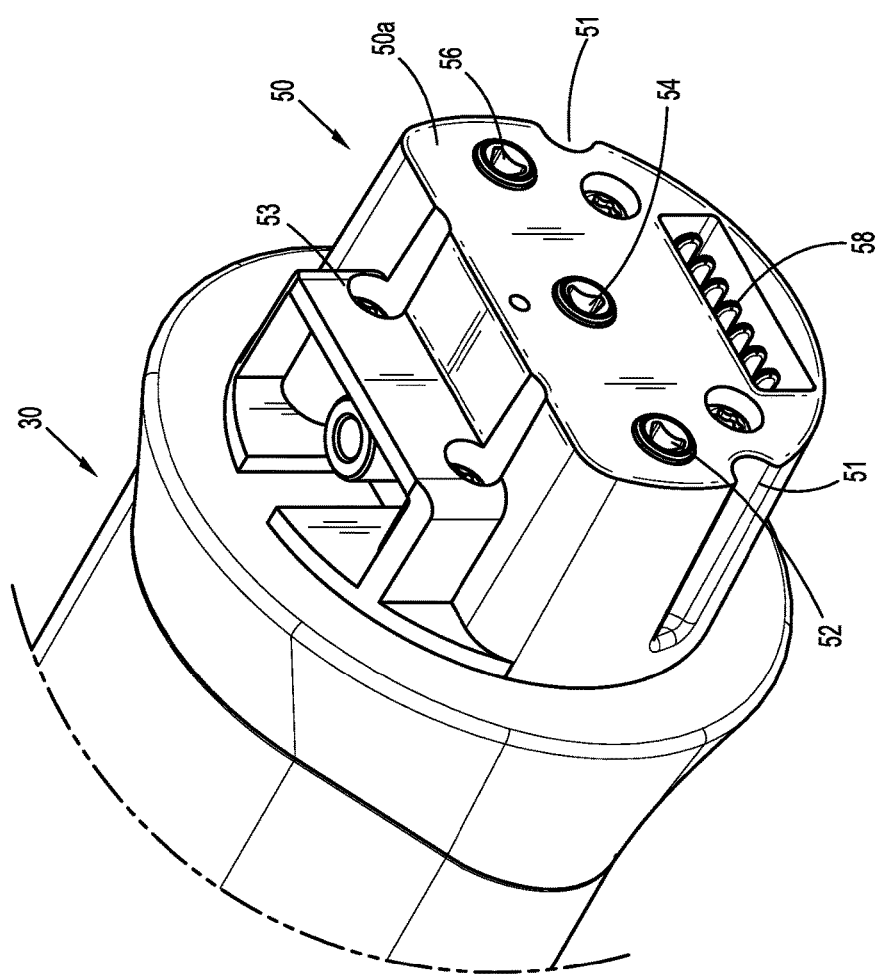
FIG. 3 is an enlarged view of the indicated area of detail of FIG. 2.

With reference to FIG. 3, the handle interface 50 of the adaptor 30 includes a cam drum input shaft 52, a lead screw input shaft 54, an articulation input shaft 56, and an interface 58 supported within the body 50a. Interface 58 is positioned on the proximal end of the adaptor 30. The body 50a of the handle interface 50 is configured to be received within the recess defined in a distal end of the receiver 24 of the handle 20 (FIG. 2). Each of the input shafts 52, 54, 56 is configured to operably engage a respective drive shaft (not shown) of the handle 20 within the receiver 24 such that actuation of the input shafts can be selectively controlled through operation of the handle 20. The handle interface 50 may define one or more interface grooves 51 and include one or more interface protrusions 53 that guide the handle interface 50 into the receiver 24 of the handle 20 and ensure that only compatible adaptors 30 are connectable to particular handles 20. The interface grooves 51 and the interface protrusions 53 may also radially align the handle interface 50 with the handle 20 such that each of the input shafts 52, 54, 56 engages a respective drive shaft of the handle 20.

The connector 58 communicates with a receiver (not shown) of the handle 20 to transmit to the handle 20 characteristics of the adaptor 30 and the loading unit 40. These characteristics of the adaptor 30 and the loading unit 40 are provided to a controller (not shown) of the handle 20 such that the handle 20 can be properly operated to control the loading unit 40. The characteristics may include, but are not limited to, the type of loading unit, the manufacturer of the loading unit, the manufacturer of the adaptor 30, the serial numbers of the loading unit or the adaptor 30, the clamping force of the jaw assembly 41, the required torque applied to each of the input shafts 52, 54, 56, the required speed of each of the input shafts 52, 54, 56, and the type of adaptor. The connector 58 may also transmit power or control signals from the handle 20 to the adaptor 30. As shown, the connector 58 is a contact connector; however, it is also contemplated that the connector 58 may be a non-contact connector, e.g., a connector that inductively transfers power or control signals.

Figure 4:
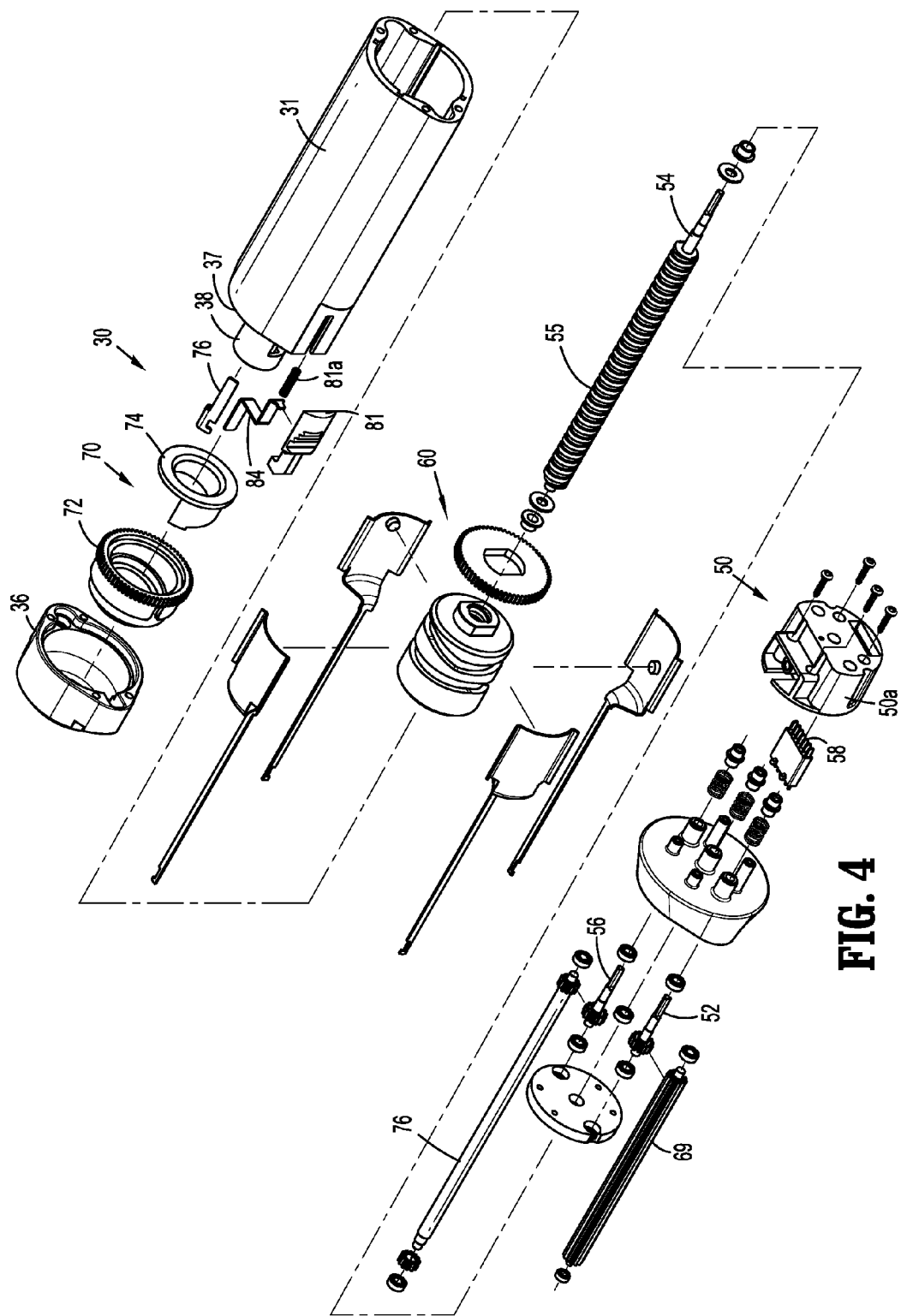
FIG. 4 is an exploded view of the stitching adaptor of FIG. 2.

Referring to FIG. 4, the adaptor 30 includes an outer casing 31, the handle interface 50, a cam drum assembly 60, and an articulation assembly 70. As illustrated, the body 50*a* of the handle interface 50 extends proximally from a proximal end of the outer casing 31. The articulation assembly 70 includes an articulation drum 72, an articulation drum 74, and an articulation shaft 76. The articulation assembly 70 is positioned adjacent a distal end of the outer casing 31 within a distal cover 36. The distal cover 36 is secured to the distal end surface 37 of the outer casing 31 over a distal end portion 38 of the outer casing 31. The articulation assembly 70 is disposed substantially between the distal end surface 37 of the outer casing 31 and the distal cover 36.

Figure 5:
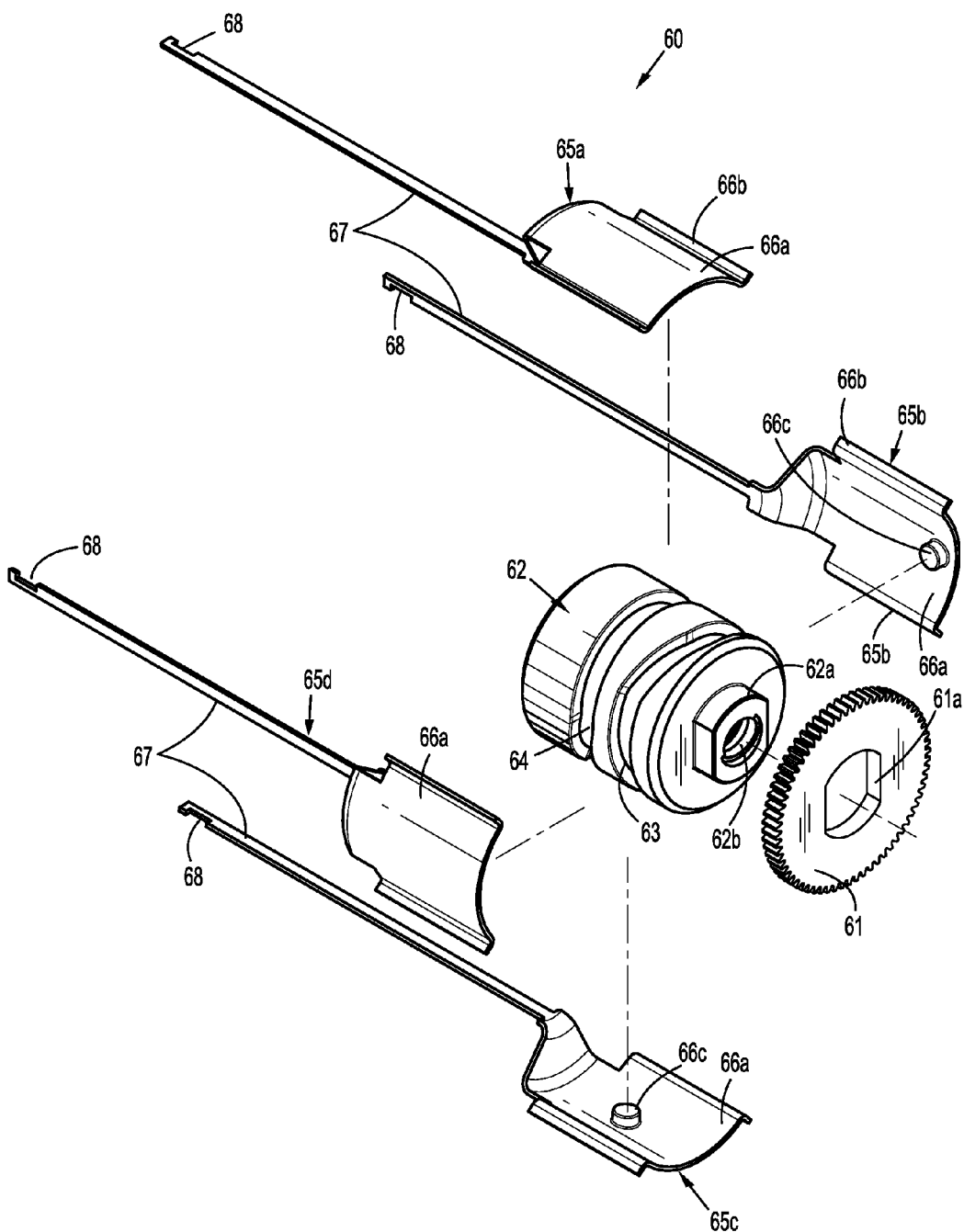
FIG. 5 is an enlarged view of the cam drum assembly of FIG. 4.
Figure 6:
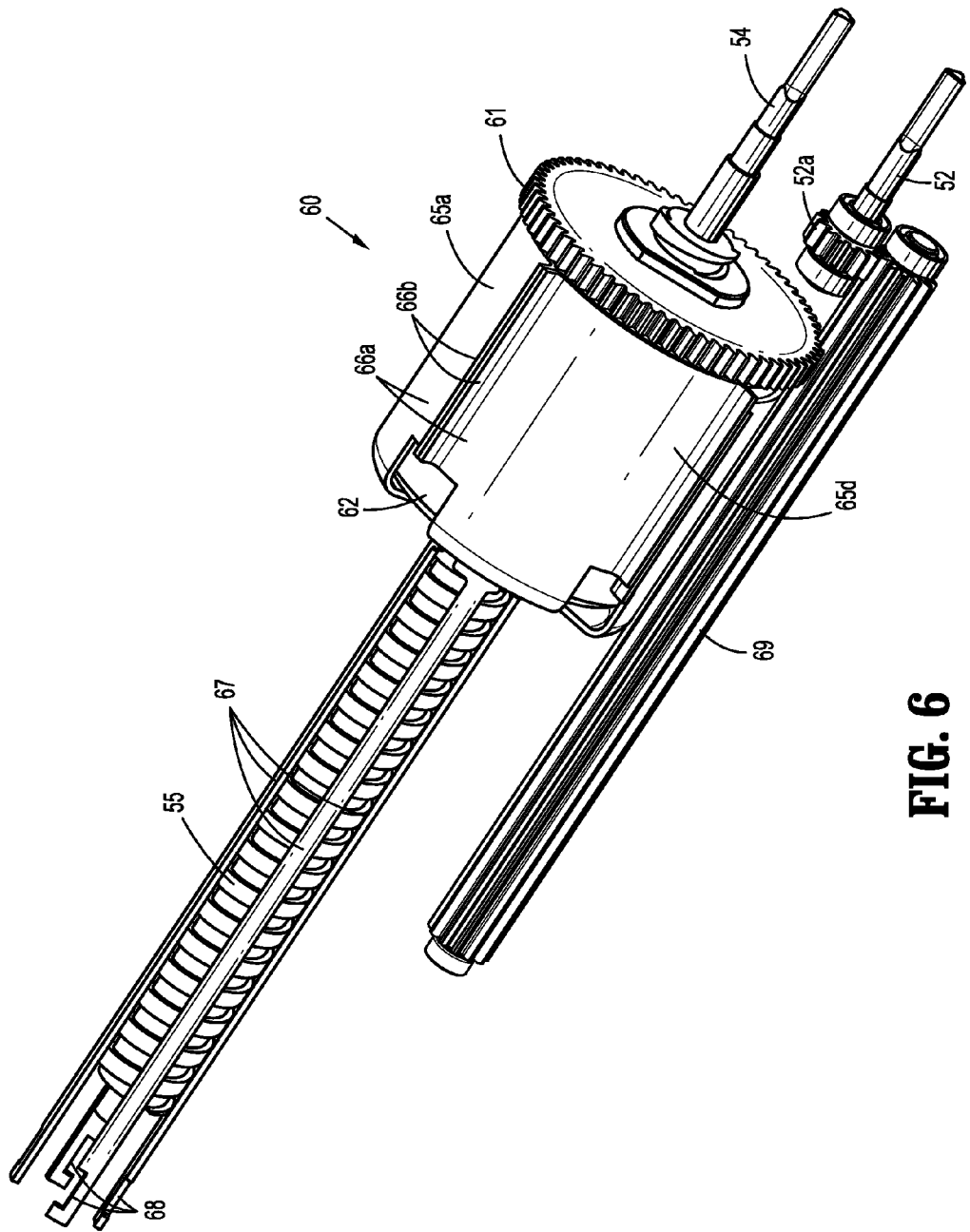
FIG. 6 is a perspective view of the cam drum assembly and the cam drum input shaft of FIG. 4 engaged in a fully retracted position.

With reference to FIGS. 5 and 6, the cam drum assembly 60 includes a cam drum gear 61, a cam drum 62, a plurality of linear drivers 65*a-d*, and a middle gear 69. The cam drum gear 61 defines a keyed opening 61*a* that mates with a raised surface 62*a* formed at a proximal end of the cam drum 62 to rotatably fix the cam drum gear 61 to the cam drum 62. The cam drum 62 is cylindrical and defines a first or proximal cam groove 63, a second or distal cam groove 64, and a threaded lead screw passage 62*b*. Each cam groove 63, 64 includes a channel disposed within the outer surface of the cam drum 62 that is configured and dimensioned to receive a cam follower 66 of one of the linear drivers 65*a-d* to facilitate longitudinal translation of the linear drivers 65*a-d* as detailed below.

Each linear driver 65*a-d* includes a proximal portion 66*a* and a linear drive arm 67. The linear drive arm 67 has a distal end which supports an engagement hook 68. The proximal portion 66*a* supports the cam follower 66 and is configured to mate with adjacent linear drivers 65*a-d* to substantially enclose the cam drum 62 within the proximal portions 66*a* of the linear drivers 65*a-d* as shown in FIG. 6. The proximal portion 66*a* of each of the linear drivers 65*a-d* may include mating flanges 66*b* that slidably engage the mating flanges 66*b* of the adjacent linear drivers 65*a-d* to facilitate linear movement of the linear drivers 65*a-d* in relation to each other along an axis parallel to the longitudinal axis of the adaptor 30.

As detailed above, the cam follower 66*c* protrudes from an inner surface of the proximal portion 66*a* of each of the linear drivers 65*a-d* and is received within one of the proximal or distal cam grooves 63, 64. The cam followers 66*c* of adjacent linear drivers 65*a-d* are positioned within different cam grooves 63, 64 and the cam followers 66*c* of opposing linear drivers 65*a-d* are positioned within the same cam grooves 63, 64. As the cam drum 62 is rotated, each cam follower 66*c* moves within a respective cam groove 63, 64 to effect longitudinal translation of a respective one of the linear drivers 65*a-d*. The linear drive arms 67 extend distally from the proximal portion 66*a* of each of the linear drivers 65*a-d* along the outer surface of the lead screw 55 (FIG. 6). The engagement hook 68 of each of the linear drivers 65*a-d* is positioned and configured to engage a drive rod of a loading unit (e.g., a drive rod 48 (FIG. 17) of the stitching loading unit 40) as detailed below.

Figure 7:
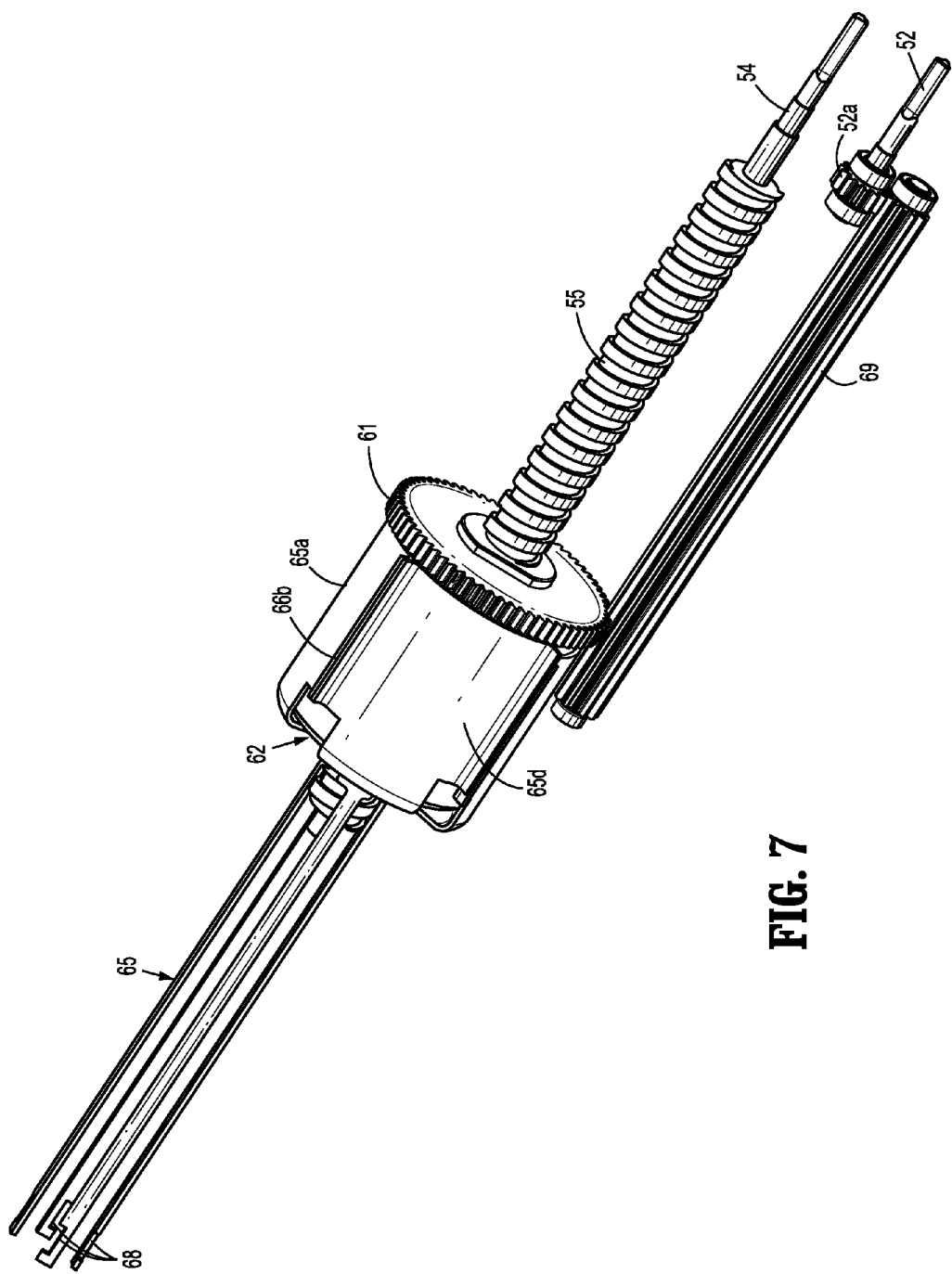
FIG. 7 is a perspective view of the cam drum assembly and the cam drum input shaft of FIG. 4 engaged in a fully extended position.

Referring also to FIG. 7, the cam drum 62 is supported about the lead screw 55 for rotation and longitudinal translation. More specifically, the lead screw 55 is disposed within the lead screw passage 62*b* of the cam drum 62. As the lead screw 55 is rotated, the cam drum 62 longitudinally translates between a fully retracted position (FIG. 6) and a fully extended position (FIG. 7). In addition, the cam drum 62 is rotatable via rotation of the cam drum gear 61 to effect longitudinal translation of the linear drivers 65*a-d* in relation to cam drum 62.

The middle gear 69 of the cam drum assembly 60 includes teeth 69*a* that extends along a length thereof. As the cam drum 62 translates between the fully retracted and extended positions, the middle gear 69 remains in continuous engagement with the cam drum gear 61 such that the cam drum input shaft 52 can effect rotation of the cam drum 62 to effect longitudinal translation of the linear drivers 65*a-d* at all the longitudinal positions of the cam drum 62.

Figure 8:
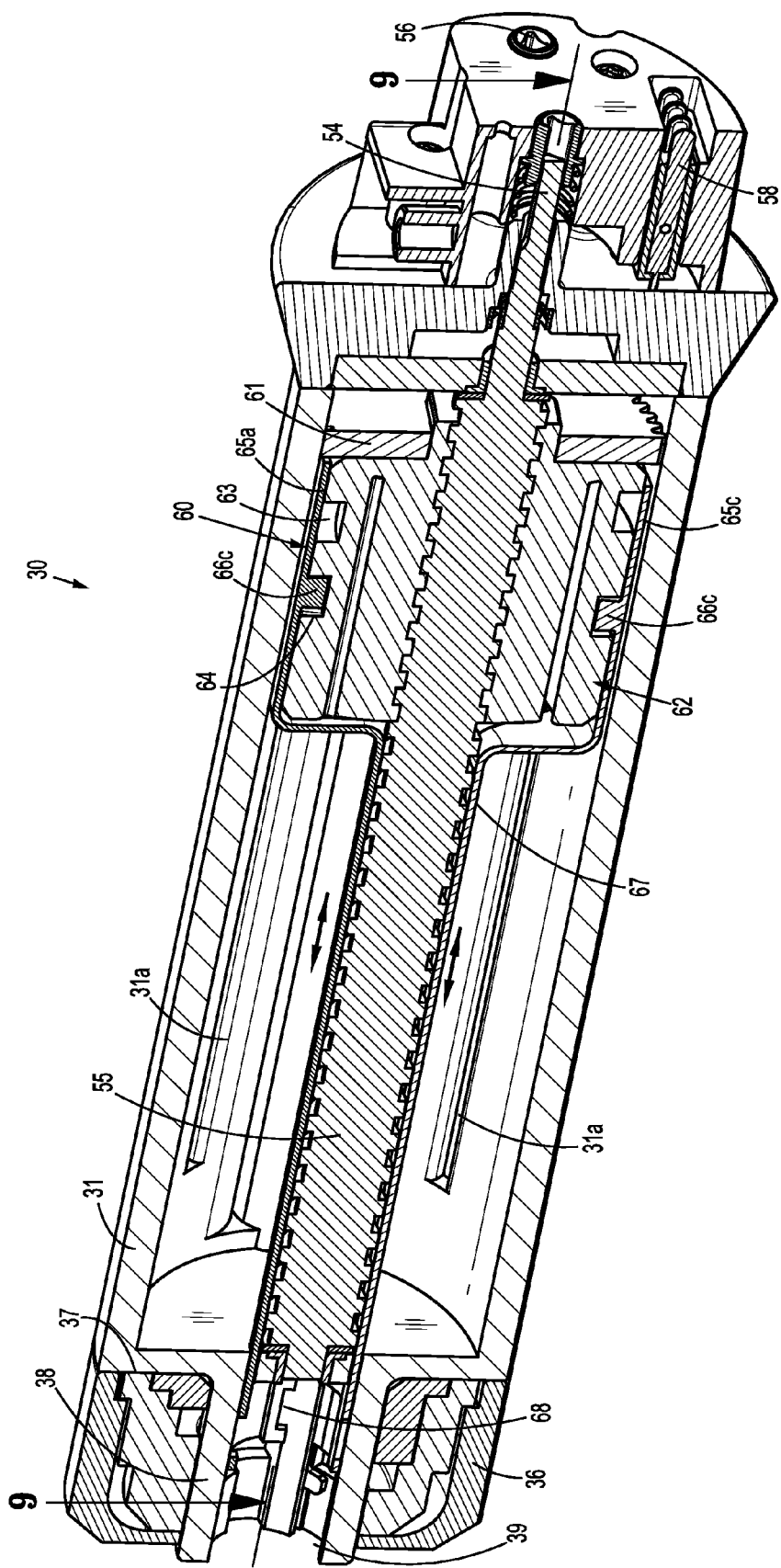
FIG. 8 is a cross-sectional view taken along section line 8-8 of FIG. 2.
Figure 9:
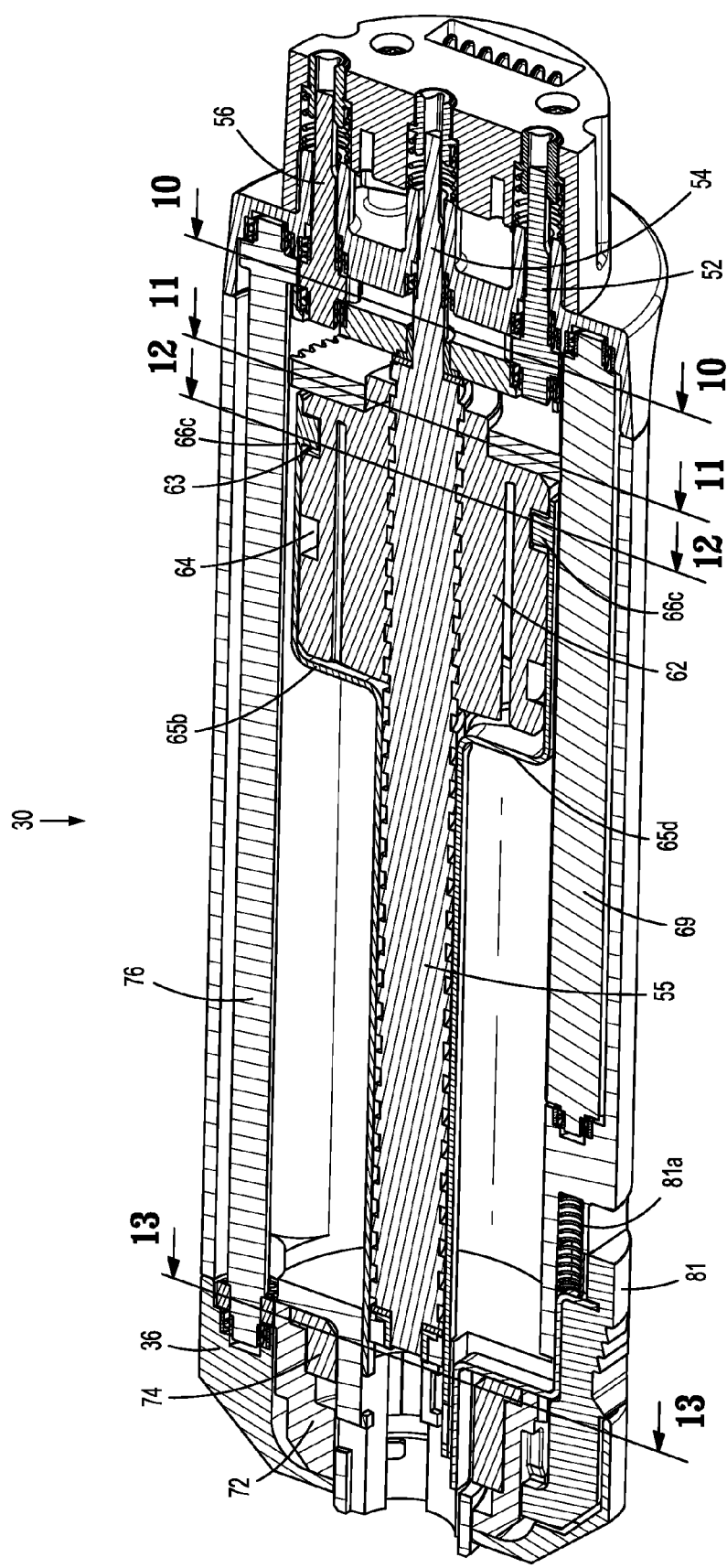
FIG. 9 is a cross-sectional view taken along section line 9-9 of FIG. 8.

With additional reference to FIG. 8, the cam drum assembly 60 is disposed within the outer casing 31 of the adaptor 30 and the linear drivers 65*a-d* of the cam drum assembly 60 are rotatably fixed relative to the outer casing 31. The inner surface of the outer casing 31 defines longitudinal alignment grooves 31*a* that receive the mating flanges 66*b* of the linear drivers 65*a-d* to rotatably fix the linear drivers 65 within the outer casing 31. The mating flanges 66*b* slide within the longitudinal alignment grooves 31*a* as the cam drum 62 translates between the fully retracted and fully extended positions and as the linear drivers 65*a-d* are advanced distally in response to rotation of the cam drum 62. When in the fully extended position, the linear drive arms 67 and the engagement hooks 68 extend from the distal end portion 38 of the outer casing 31.

Referring now to FIGS. 8-13, the adaptor 30 converts the rotation of the input shafts 52, 54, 56 (FIG. 9) into longitudinal translation of the linear drivers 65*a-d*, the cam drum 62, and/or the articulation arm 78. The lead screw input shaft 54 engages the lead screw 55 to effect longitudinal translation of the cam drum 62 within the outer casing 31 as detailed above. In embodiments, the lead screw input shaft 54 and the lead screw 55 are integrally formed. When the cam drum 62 longitudinally translates, the mating flanges 66*b* of the linear drivers 65*a-d* are disposed within the longitudinal alignment grooves 31*a* of the outer casing 31 to rotatably fix the linear drivers 65*a-d*. As detailed above, the cam followers 66*c* of the linear drivers 65*a-d* are received within the cam grooves 63, 64 of the cam drum 62 such that upon rotation of the cam drum 62 the linear drivers 65*a-d* translate longitudinally relative to the cam drum 62 as detailed below.

As illustrated, the linear driver 65*a* and 65*b* define a first pair of linear drivers and the linear drivers 65*c* and 65*d* define a second pair of linear drivers. In this embodiment, the linear drivers of the first pair of linear drivers 65*a*, 65*b* are positioned adjacent to one another; however, it is also within the scope of this disclosure for the linear drivers of the first and second pair of linear drivers to oppose one another. The first pair of linear drivers 65*a*, 65*b* is associated with components of the first jaw member 43*a* (FIG. 1) and the second pair of linear driver 65*c*, 65*d* is associated with components of the second jaw member 43*b* (FIG. 1). The cam follower 66*c* of one of the linear drivers of each pair of linear drivers (e.g., 65*a*, 65*c*) is disposed within the distal cam groove 64 and the cam follower 66*c* of the other one of the linear drivers of each pair of linear drivers (e.g., 65*b*, 65*d*) is disposed within the proximal cam groove 63.

As the cam drum 62 rotates, the cam follower 66*c* moves within a respective cam groove 63, 64 to effect longitudinal advancement and retraction of the linear drivers 65*a-d* relative to the outer casing 31. The pitch of each of the cam grooves 63, 64 is configured to cycle (i.e., advance and retract) the linear drivers 65*a-d* to manipulate drive rods of a loading unit (e.g., a drive rods 48 (FIG. 17) of the stitching loading unit 40) to manipulate components within the jaw assembly 41 of the loading unit 40 (FIG. 1). A full rotation of the cam drum 62 may effect one longitudinal advancement and refraction of each of the linear drivers 65a-d or may effect multiple longitudinal advancements and retractions of each of the linear drivers 65a-d.

A full cycle of each of the first and second pairs of linear drivers 65a, 65b and 65c, 65d includes four phases of movement. In a first phase of movement, both of the linear drivers of the pair of linear drivers (e.g., the linear drivers 65a, 65b) are advanced together in substantial alignment with one another. In a second phase of movement, a first driver of the pair of linear drivers (e.g., the linear driver 65a) is longitudinally fixed relative to the outer casing 31 and a second driver of the pair of linear drivers (e.g., the linear driver 65b) is longitudinally advanced relative to the outer casing 31. In a third phase of movement, the first driver of the pair of linear drivers (e.g., the linear driver 65a) remains longitudinally fixed within the outer casing 31 and the second linear driver of the pair of linear drivers (e.g., the linear driver 65b) is retracted within the outer casing 31 to move the second linear driver into substantial alignment with the first linear driver. In a fourth phase, both of the linear drivers of the pair of linear drivers (e.g., the linear driver 65a, 65b) are longitudinally fixed relative to the outer casing 31. It will be understood, that a full cycle of the second pair of linear drivers 65c, 65d is as detailed above with regard to the linear drivers 65a, 65b.

In embodiments, when the first pair of linear drivers 65a, 65b is in the first phase of movement, the second pair of linear drivers 65c, 65d are in the fourth phase of movement. The first, second, and third phases of movement may be substantially equal in duration and the fourth phase of movement may account for a duration equal to the sum of the duration of the first three phases of movement. As one of the pairs of linear drivers cycles through the first three phases of movement, the other one of the pairs of linear drivers is in the fourth phase of movement. In some embodiments, as the first pair of linear drivers 65a, 65b begins the third phase of movement the second pair of linear drivers 65c, 65d begins the first phase of movement. In such embodiments, each of the four phases of movement may be substantially equal in duration.

The pitch of each of the cam grooves 63, 64 may be configured to cycle the linear drivers 65a-d as the lead screw 55 effects constant advancement of the cam drum 62. It is also contemplated that the lead screw 55 may be intermittently rotated to intermittently advance the cam drum 62 (i.e., in a stepwise manner) and the pitch of the cam grooves 63, 64 may be configured cycle the linear drivers 65a-d as the lead screw 55 effects intermittent advancement of the cam drum 62.

The cam drum input shaft 52 (FIG. 9) has a distal end supporting a drive gear 52a. As best shown in FIG. 10, the drive gear 52a engages the teeth 69a of a middle gear 69 such that the middle gear 69 rotates in response to rotation of the input shaft 52. The teeth 69a of the middle gear 69 engage the cam drum gear 61 such that the cam drum gear 61 rotates in response to rotation of the cam drum input shaft 52 as shown in FIG. 11. It will be appreciated that the cam drum 62 rotates in the same radial direction as the cam drum input shaft 52 and the middle gear 69 rotates in the opposite radial direction.

The articulation input shaft 56 (FIG. 9) has a distal end supporting a drive gear 56a. The articulation shaft 76 (FIG. 9) has a proximal end supporting a proximal gear 76a. With reference to FIGS. 10 and 11, the drive gear 56a of the articulation input shaft 56 engages the proximal gear 76a of the articulation shaft 76 to effect rotation of the articulation shaft 76 in response to rotation of the articulation input shaft 56.

Figure 13:
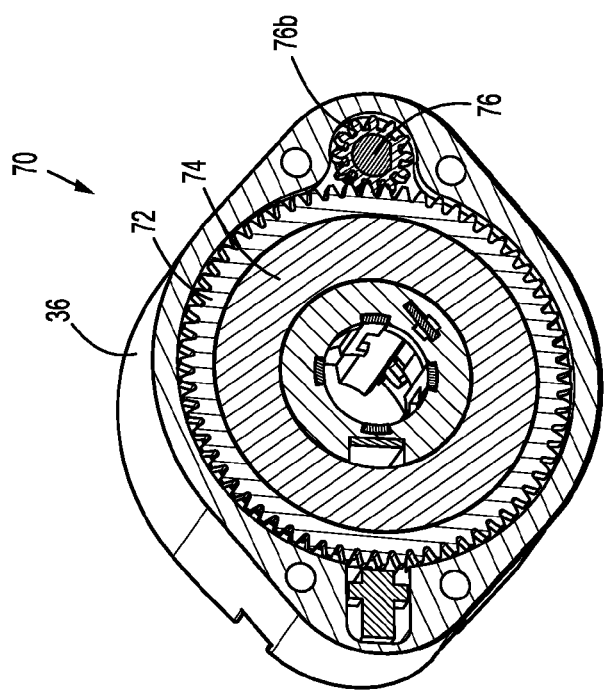
FIG. 13 is a cross-sectional view taken along section line 13-13 of FIG. 9.
Figure 12:
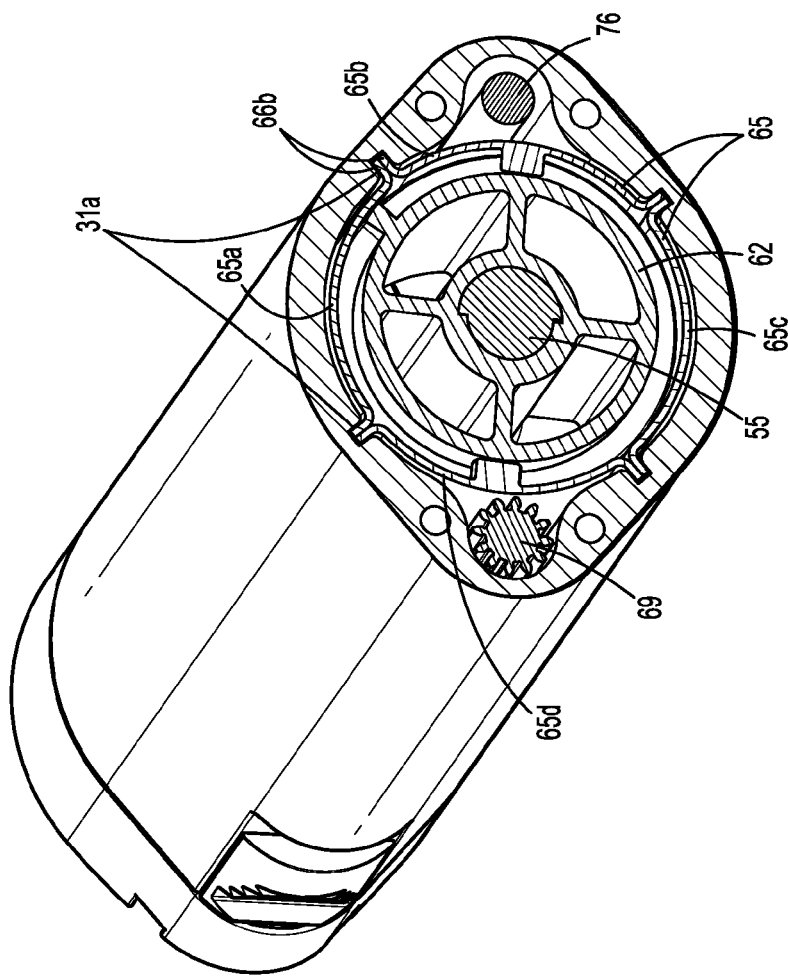
FIG. 12 is a cross-sectional view taken along section line 12-12 of FIG. 9.

As shown in FIG. 13, the articulation shaft 76 has a distal end supporting a distal gear 76b. The distal gear 76 engages teeth on the outer surface of the articulation drum 72 to rotate the articulation drum 72 in response to the rotation of the articulation input shaft 56. It will be appreciated that the articulation drum 72 rotates in the same radial direction as the articulation input shaft 56 and the articulation shaft 76 rotates in the opposite radial direction to that of the input shaft 56. It is further appreciated, that a portion of the articulation shaft 76 positioned between the proximal and distal gears 76a, 76b is dimensioned to prevent the articulation shaft 76 from interfering with the cam drum gear 61 as the cam drum 62 is translated within the outer casing 31 as shown in FIGS. 11 and 12.

Figure 14:
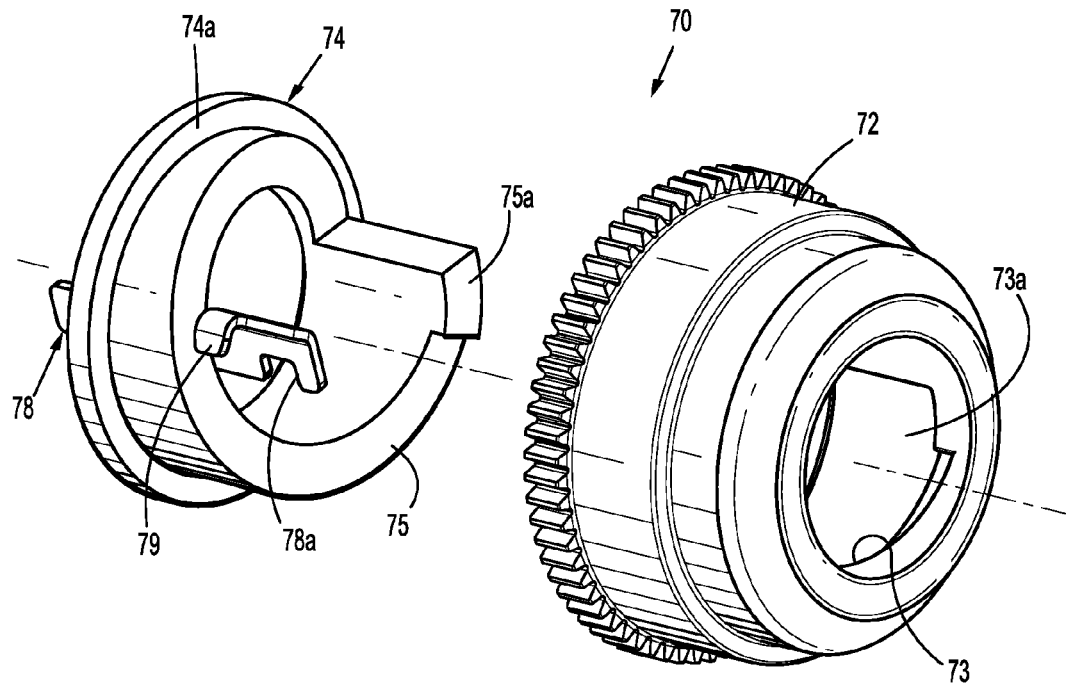
FIG. 14 is a front perspective view of the articulation assembly of FIG. 4 with the parts separated.
Figure 15:
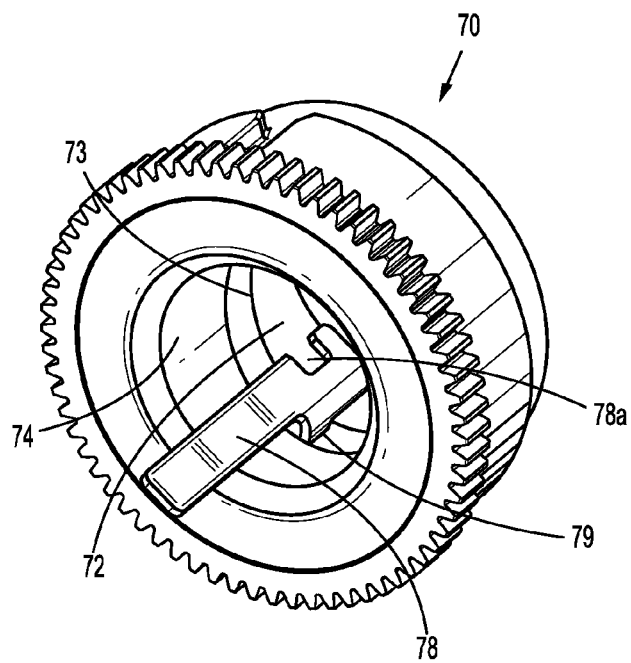
FIG. 15 is a rear perspective view of the articulation assembly of FIG. 4.

With reference to FIGS. 13-15, the articulation assembly 70 includes the articulation drum 72, the articulation cam 74, and an articulation drive bar 78. The articulation drive bar 78 includes an articulation hook 78a configured to engage an articulation rod 48 of the stitching loading unit 40 (FIG. 17) as detailed below. The articulation drum 72 and the articulation cam 74 are substantially cylindrical. The articulation cam 74 is disposed within the articulation drum 72 and includes a proximal flange 74a. The proximal flange 74a engages a surface of the articulation drum 72 to longitudinally fix the articulation cam 74 relative to the articulation drum 72. The articulation cam 74 includes a proximal camming surface 75 and an articulation key 75a. The articulation key 75a extends from the proximal camming surface 75 and is received within an articulation keyway 73a defined in an inner surface of the articulation drum 72. The cooperation of the articulation key 75a and the articulation keyway 73a rotationally fixes the articulation cam 74 to the articulation drum 72 such that rotation of the articulation cam 74 is effected by rotation of the articulation drum 72.

The proximal camming surface 75 of the articulation cam 74 is a helical surface configured to slidably engage an articulation cam follower 79 of the articulation drive bar 78 such that rotational movement of the articulation cam 74 effects advancement of the articulation drive bar 78. The articulation drum 72 includes a helical distal camming surface 73 that is configured to slidably engage the articulation cam follower 79 such that rotational movement of the articulation drum 72 effects rotation of the articulation drive bar 78. The camming surfaces 73, 75 have a substantially similar profile such that the articulation cam follower 79 is retained between the camming surfaces 73, 75. As the as the articulation drum 72 rotates in a first direction (e.g., counterclockwise when viewed from the proximal end), the cam follower 79 is advanced and as the articulation drum 72 is rotated in a second opposite direction (e.g., clockwise when viewed from the proximal end), the articulation cam follower 79 is retracted. The articulation assembly 70 includes a plurality of articulated positions between a first articulated position and a second articulated position. The articulation assembly 70 also includes a straight position substantially halfway between the first and second articulated positions.

Referring to FIGS. 16-28, the adaptor 30 is secured to a connector of a loading unit (e.g., the connector 44 of the stitching loading unit 40) by a locking mechanism 80 of the adapter 30.

Figure 18:
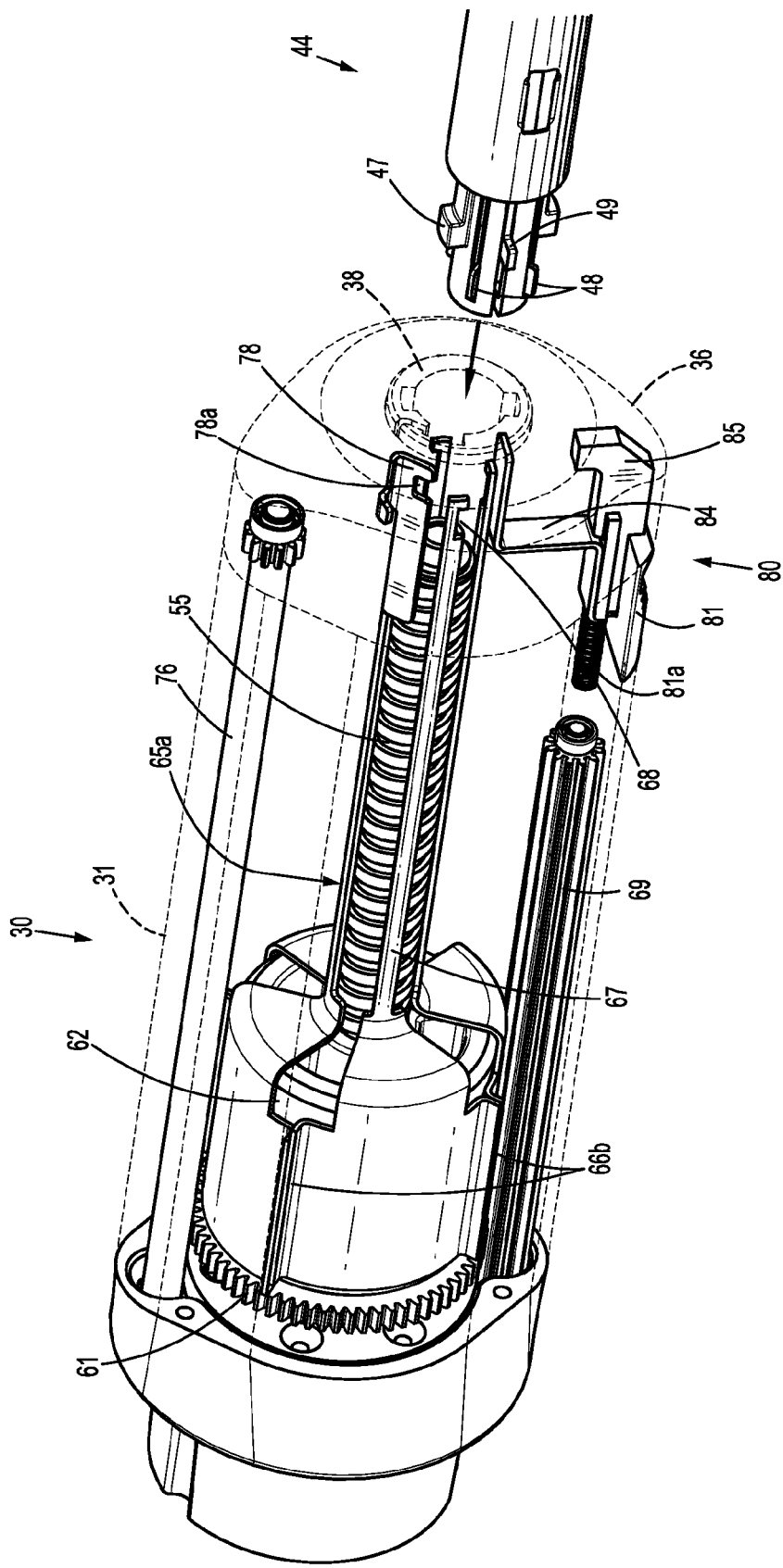
FIG. 18 is a cut-away view of the stitching adaptor.

With particular reference to FIGS. 17 and 18, a proximal portion of the stitching loading unit 40 includes a connector 44. The connector 44 includes guide lugs 47, drive rods 48, and an articulation rod 49.

Figure 19:
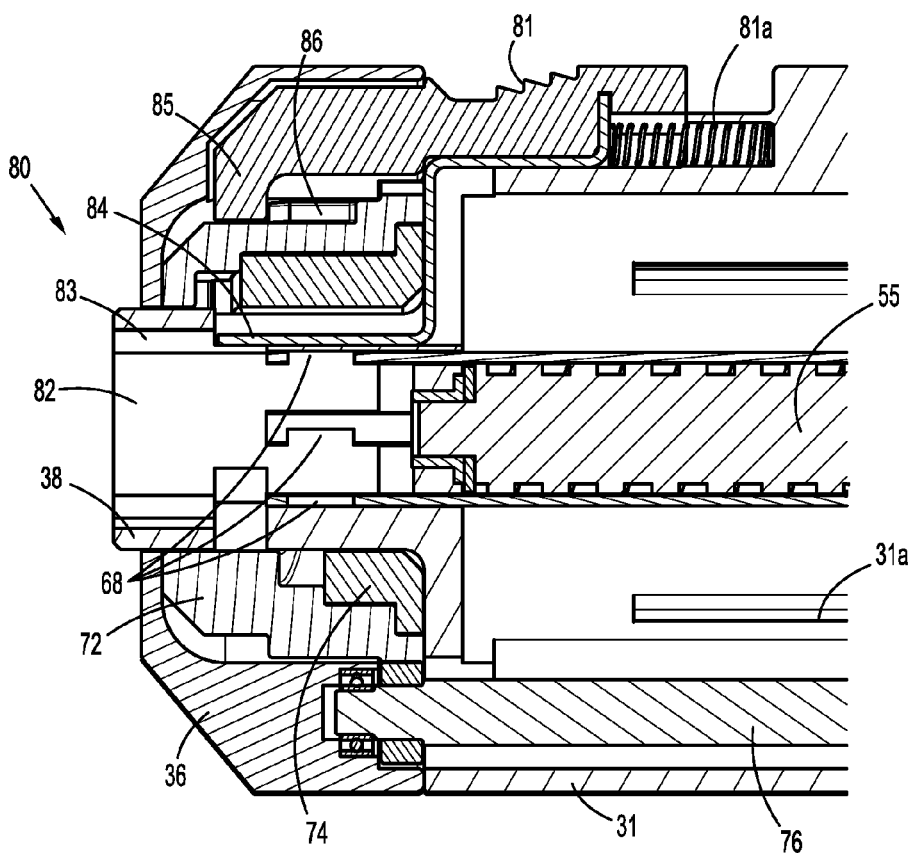
FIG. 19 is a cross-sectional view taken along section line 19-19 of FIG. 17.
Figure 20:
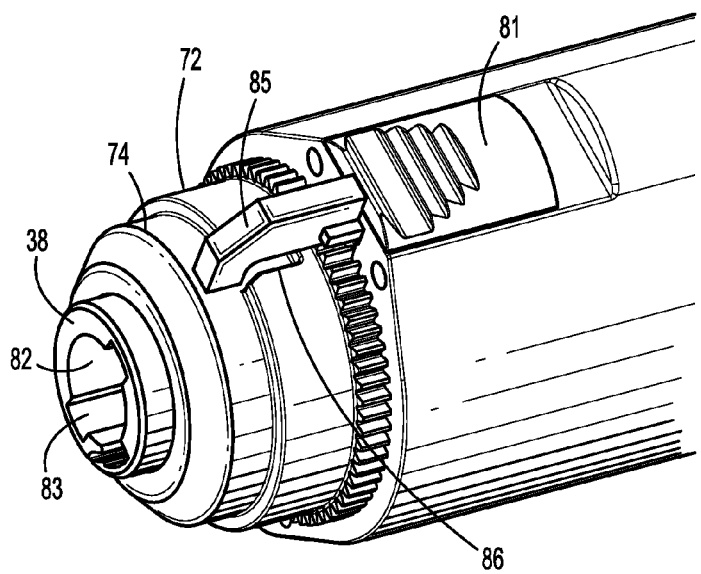
FIG. 20 is a front perspective view of the distal end portion of the stitching adaptor of FIG. 17 with the distal cover removed.
Figure 21:
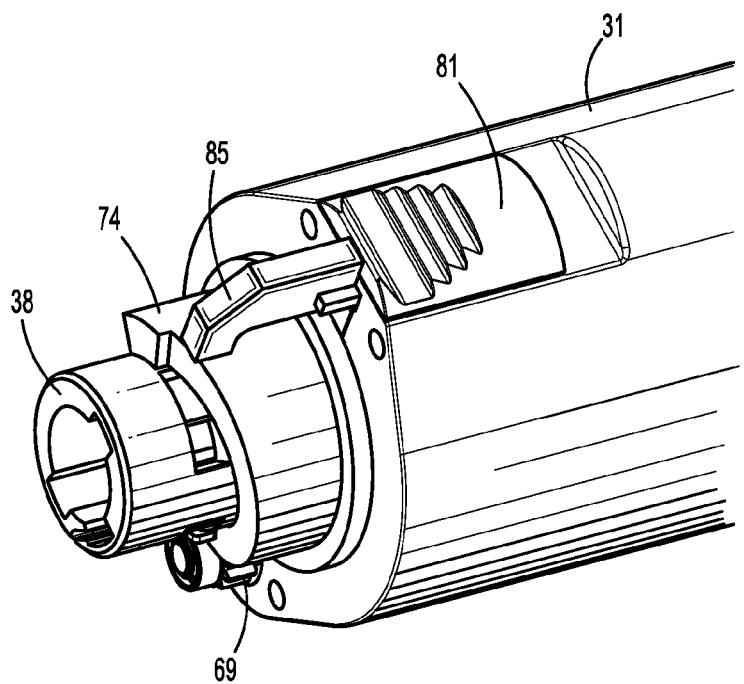
FIG. 21 is a front perspective view of the distal end of the stitching adaptor of FIG. 20 with the articulation drum removed.

Referring also to FIG. 19, the locking mechanism 80 is disposed substantially within the distal cover 36 of the adaptor 30 and includes a release switch 81 (FIG. 18) disposed on an outer surface of the outer casing 31. A distal end portion 38 of the outer casing 31 defines a locking opening 82 and locking grooves 83. The release switch 81 includes a lock arm 85 extending distally therefrom. A switch-biasing member 81a is operatively associated with the release switch 81 to urge the release switch 81 distally. A lock bar 84 is operatively associated with the release switch 81 such that longitudinal advancement or retraction of the release switch 81 effects longitudinal advancement or retraction of the lock bar 84 and longitudinal advancement or retraction of the lock bar 84 effects longitudinal advancement or retraction of the release switch 81 as detailed below. The lock bar 84 is disposed in one of the locking grooves 83. The articulation drum 72 defines an articulation interlock groove 86 that is aligned with the lock arm 85 when the articulation assembly 70 is in the straight configuration as shown in FIG. 20. A portion of the lock arm 85 may be in contact with the outer surface of the articulation cam 74 as shown in FIG. 21.

Figure 22:
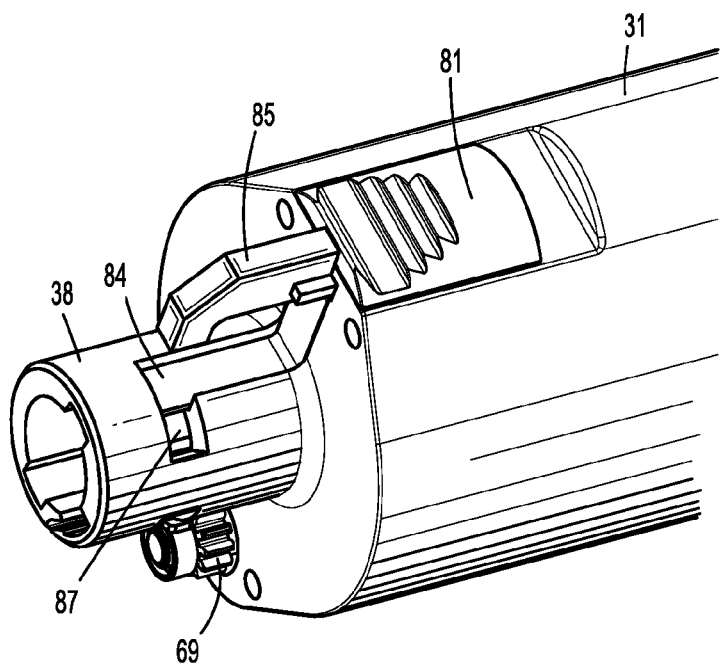
FIG. 22 is a front perspective view of the distal end of the stitching adaptor of FIG. 21 with the articulation cam removed.
Figure 23:
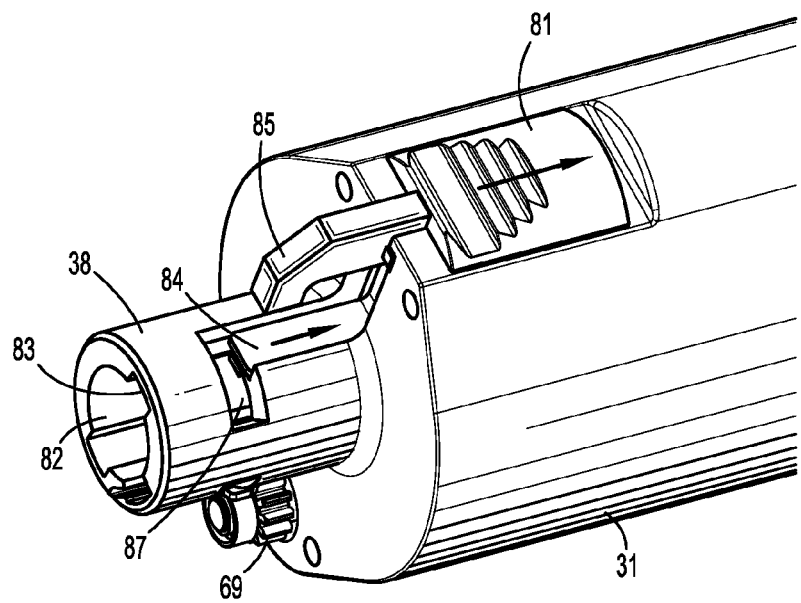
FIG. 23 is a front perspective view of the distal end of the stitching adaptor of FIG. 22.
Figure 24:
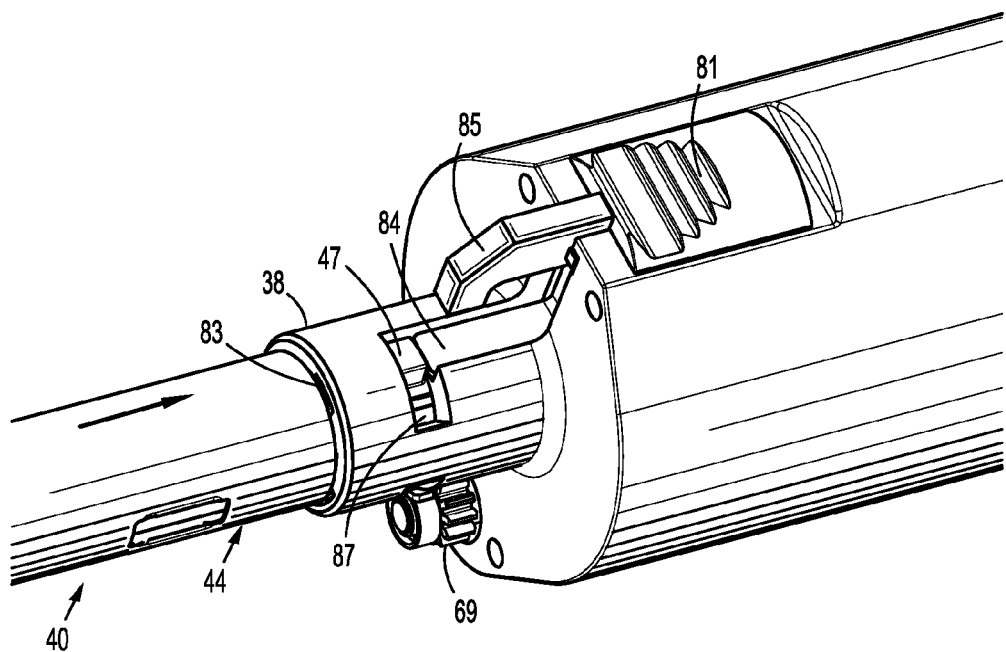
FIGS. 24-26 are a progression of front perspective views of the stitching loading unit of FIG. 16 being secured to the stitching adaptor of FIG. 23.

With particular reference to FIGS. 22-24, the distal end portion 38 of the outer casing 31 defines a lug lock 87 in communication with the locking groove 83. The lock arm 85 is disposed within the locking groove 83. The locking mechanism 80 has a locked configuration (FIG. 22) and an open configuration (FIG. 23). In the locked configuration, the lock bar 84 extends within the locking groove 83 past the lug lock 87. The switch biasing member 81a (FIG. 19) biases the locking mechanism 80 towards the locked configuration. The release switch 81 may be engaged by a clinician to move the release switch 81 proximally against the switch-biasing member 81a as shown in FIG. 23 or one of the guide lugs 47 may engage the lock bar 84 to move the lock bar 84 proximally to the unlocked configuration. It will be appreciated that the lock arm 85 must be aligned with the articulation lock groove 86 (FIG. 20) for the locking mechanism 80 to transition to the unlocked configuration (i.e., the articulation assembly must be in the straight configuration). For example, if the articulation assembly 70 is in the first or second articulated configurations, the articulation drum 72 will be positioned such that the articulation lock groove 86 will not be aligned with the lock arm 85 to prevent the locking mechanism 80 from transitioning to the unlocked configuration. Moreover, when the locking mechanism 80 is in the unlocked configuration, the lock arm 85 will prevent the articulation drum 72 from rotating and will prevent the articulation assembly 70 from transitioning to the straight configuration.

Figure 25:
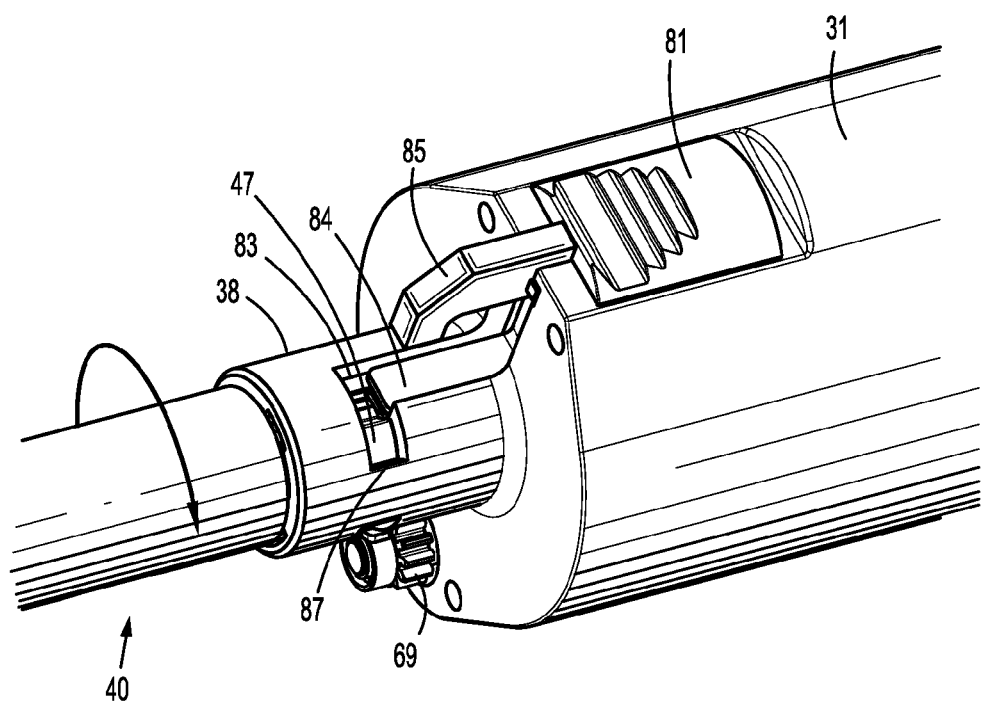
Figure 26:
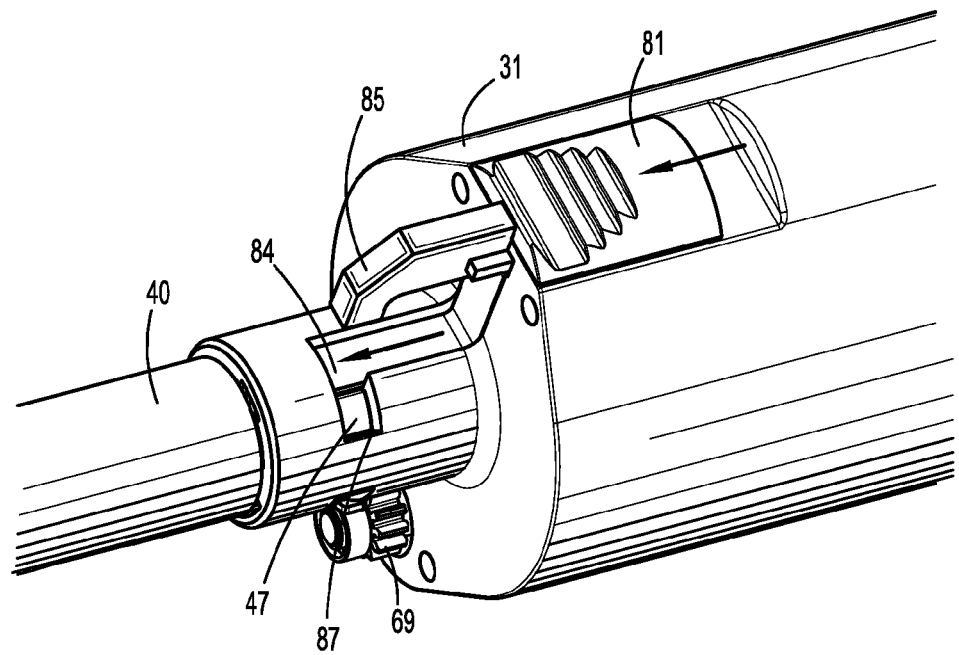

When the connector 44 of the stitching loading unit 40 engages the adaptor 30, the guide lugs 47 are aligned with the locking grooves 83. As shown in FIG. 24, when the guide lugs 47 slide proximally within the locking grooves 83, one of the guide lugs 47 may engage the lock bar 84 to urge the locking mechanism 80 to the unlocked configuration. When the guide lugs 47 abut the lock bar 84 in the unlocked configuration, the stitching loading unit 40 is rotated relative to the adaptor 30 to rotate the guiding lug 47 into the lug lock 87 as shown in FIG. 25. The locking mechanism 80 then returns to the locked configuration such that the lock bar 84 extends within the locking groove 83 to capture the guiding lug 47 within the lug lock 87 as shown in FIG. 26.

Figure 27:
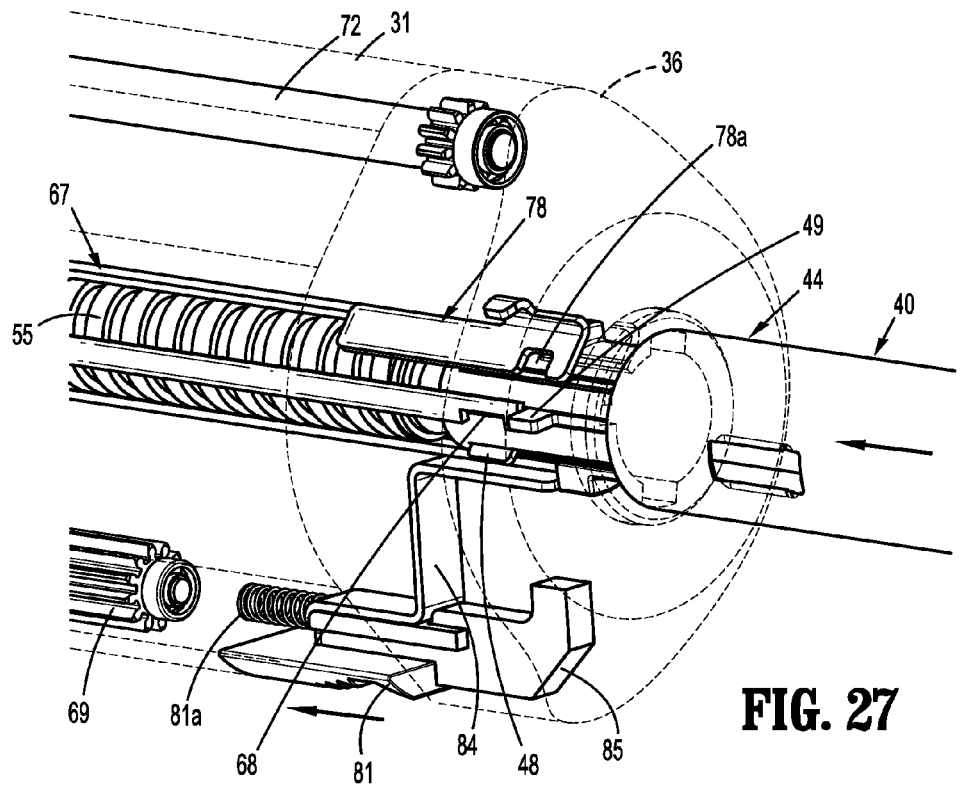
FIG. 27 is a cut-away view of the stitching adaptor and the stitching loading unit of FIG. 24.
Figure 28:
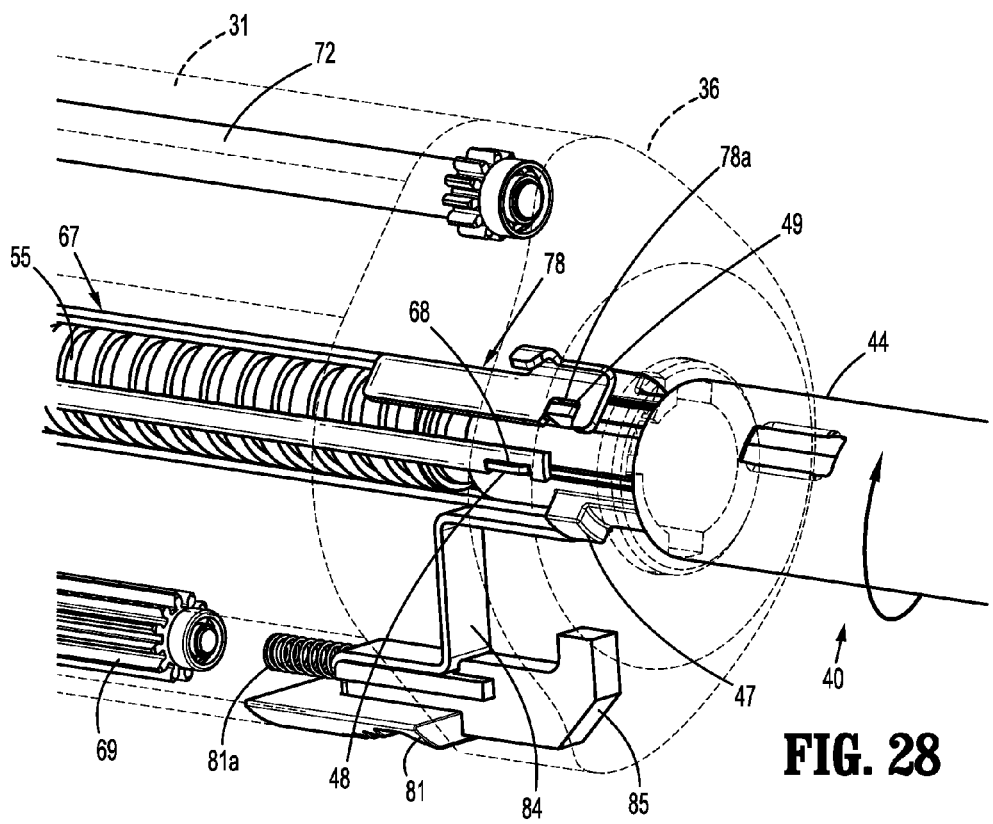
FIG. 28 is a cut-away view of the stitching adaptor and the stitching loading unit of FIG. 25.

With reference to FIGS. 27 and 28, when the stitching loading unit 40 is inserted into the adaptor 30, the drive rods 48 and the articulation rod 49 are captured by the engagement hooks 68 of the linear drive arms 67 and the articulation hook 78a of the articulation drive arm 78 respectively. When the guide lugs 47 are aligned in the locking grooves 83, the drive rods 48 are offset from the engagement hooks 68 and the articulation rod 49 is offset from the articulation hook 78a as shown in FIG. 27. When the stitching loading unit 40 is rotated to secure the guiding lug 47 within the lug lock 87 as shown in FIG. 25, the drive rods 48 are captured in the engagement hooks 68 and the articulation rod 49 is captured in the articulation hook 78a as shown in FIG. 28. When the rods 48, 49 are captured within the hooks 68, 78a, longitudinal translation of the hooks 68, 78a effects longitudinal translation of the rods 48, 49 as detailed above to manipulate components of the stitching loading unit 40.

The stitching loading unit 40 can be released from the adaptor 30 by retracting the release switch 81 against the switch-biasing member 81a as shown in FIG. 23. With the release switch 81 retracted, the stitching loading unit 40 is rotated to move the guide lug 47 out of the lug lock 87. With the guide lug 47 out of the lug lock 87, the stitching loading unit 40 is free to be removed from the adaptor 30. The switch 81 may be released when the guide lug 47 is within the locking groove 83 such that the lock bar 84 is advanced by the switch-biasing member 81a to disengage the stitching loading unit 40 from the adaptor 30. Another loading unit may then be secured to the adaptor 30.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. An adaptor for a powered surgical instrument, the adaptor comprising:
    a casing; a cam drum disposed within the casing and defining a longitudinal axis, the cam drum being translatable along the longitudinal axis between a retracted position and an advanced position in relation to the casing, the cam drum being supported for rotation about the longitudinal axis and defining first and second radial cam grooves about an outer surface thereof, the first cam groove defining a first profile and the second cam groove defining a second profile; a first linear driver including a first cam follower disposed in the first cam groove, the first linear driver being supported for movement between advanced and retracted positions in relation to the cam drum along an axis parallel to the longitudinal axis in response to rotation of the cam drum about the longitudinal axis; and a second linear driver including a second cam follower disposed in the second cam groove, the second linear driver being supported for movement between advanced and retracted positions in relation to the cam drum along an axis parallel to the longitudinal axis in response to rotation of the cam drum about the longitudinal axis.

2. The adaptor of claim 1, further comprising a lead screw rotatable about the longitudinal axis, the lead screw being received within a lead screw passage defined by the cam drum, wherein rotation of the lead screw effects longitudinal translation of the cam drum and the first and second linear drivers along the longitudinal axis.

3. The adaptor of claim 1, wherein the second cam groove is positioned distal to the first cam groove.

4. The adaptor of claim 1, further comprising an articulation assembly including an articulation shaft, an articulation drum, an articulation cam, and an articulation arm, the articulation shaft extending along an axis parallel to the longitudinal axis and being engaged with the articulation drum to effect rotation of the articulation drum when the articulation shaft is rotated, the articulation cam being disposed within the articulation drum, the articulation cam and the articulation drum being radially fixed relative to one another, the articulation cam defining a proximal camming surface and the articulation drum defining a distal camming surface, the articulation arm including an articulation cam follower disposed between the proximal and distal camming surfaces such that as the articulation drum and the articulation cam are rotated about the longitudinal axis, the articulation arm is longitudinally translated between a first articulated position, a straight position, and a second articulated position.

5. The adaptor of claim 4, wherein in the straight configuration of the articulation arm is about halfway between the first and second articulated positions of the articulation arm.

6. The adaptor of claim 1, wherein the first and second linear drivers define a first pair of linear drivers and as the cam drum is rotated the first and second profiles of the first and second cam grooves translate the first pair of linear drivers through a cycle, the cycle having a first phase of movement, wherein the first and second linear drivers are longitudinally advanced in relation to the casing, a second phase of movement, wherein the first linear driver is longitudinally fixed in relation to the casing and the second linear driver is longitudinally advanced in relation to the casing, a third phase of movement, wherein the first linear driver is longitudinally fixed and the second linear driver is longitudinally retracted in relation to the casing, and a fourth phase of movement, wherein the first and second linear drivers are both longitudinally fixed in relation to the casing.

7. The adaptor of claim 6, further comprising a second pair of linear drivers including:
   a third linear driver including a third cam follower disposed in the first cam groove, the third linear driver being supported for movement between advanced and retracted positions in relation to the cam drum along an axis parallel to the longitudinal axis in response to rotation of the cam drum about the longitudinal axis; and
   a fourth linear driver including a fourth cam follower disposed in the second cam groove, the fourth linear driver being supported for movement between advanced and retracted positions in relation to the cam drum along an axis parallel to the longitudinal axis in response to rotation of the cam drum about the longitudinal axis, wherein as the cam drum is rotated the first and second profiles of the first and second cam grooves translate the second pair of linear drivers through the cycle.

8. The adaptor of claim 7, wherein the third linear driver is positioned about the cam drum in opposed relation to the first linear driver and the fourth linear driver is positioned about the cam drum in opposed relation to the second linear driver.

9. The adaptor of claim 8, wherein the first, second, third, and fourth cam followers are positioned in the first or second cam grooves such that when the first pair of linear drivers begins the first phase of movement, the second pair of linear drivers is in the fourth phase of movement.

10. The adaptor of claim 8, wherein the first, second, third, and fourth cam followers are positioned in the first or second cam grooves such that when the first pair of linear drivers begins the third phase of movement, the second pair of linear drivers begins the first phase of movement.

11. An adaptor for a powered surgical instrument, the adaptor comprising:
   a casing;
   a cam drum defining a longitudinal axis, the cam drum being translatable along the longitudinal axis between a retracted position and an advanced position in relation to the casing, the cam drum being supported for rotation about the longitudinal axis and defining first and second radial cam grooves about an outer surface thereof, the first cam groove defining a first profile and the second cam groove defining a second profile;
   a first linear driver including a first cam follower disposed in the first cam groove, the first linear driver being supported for movement between advanced and retracted positions in relation to the cam drum along an axis parallel to the longitudinal axis in response to rotation of the cam drum about the longitudinal axis;
   a second linear driver including a second cam follower disposed in the second cam groove, the second linear driver being supported for movement between advanced and retracted positions in relation to the cam drum along an axis parallel to the longitudinal axis in response to rotation of the cam drum about the longitudinal axis; and
   a cam drum gear coupled to the cam drum such that rotation of the cam drum gear effects rotation of the cam drum.

12. The adaptor of claim 11, further comprising a middle gear and a cam drum input shaft, the middle gear and the cam drum input shaft being rotatably disposed about axes which are parallel to the longitudinal axis, the cam drum input shaft being engaged with the middle gear and the middle gear being engaged with the cam drum gear such that rotation of the cam drum input shaft effects rotation of the cam drum.

13. The adaptor of claim 12, wherein the middle gear is in continuous engagement with the cam drum input shaft and the cam drum gear as the cam drum is longitudinally translated between the retracted and the advanced positions.

14. A powered surgical instrument comprising:
   a handle including a receiver;
   an adaptor defining a longitudinal axis and including:
      a casing having proximal and distal end portions;
      a handle interface disposed in the proximal end portion, the handle interface releasably coupled to the receiver of the handle;
      a cam drum being translatable along the longitudinal axis between a retracted position and an advanced position in relation to the casing, the cam drum being supported for rotation about the longitudinal axis and defining first and second radial cam grooves about an outer surface thereof, the first cam groove defining a first profile and the second cam groove defining a second profile;
      a first pair of linear drivers including:
         a first linear driver including a first cam follower disposed in the first cam groove, the first linear driver being supported for movement between advanced and retracted positions in relation to the cam drum along an axis parallel to the longitudinal axis in response to rotation of the cam drum about the longitudinal axis; and a second linear driver including a second cam follower disposed in the second cam groove, the second linear driver being supported for movement between advanced and retracted positions in relation to the cam drum along an axis parallel to the longitudinal axis in response to rotation of the cam drum about the longitudinal axis;

a second pair of linear drivers including:

a third linear driver including a third cam follower disposed in the first cam groove, the third linear driver being supported for movement between advanced and retracted positions in relation to the cam drum along an axis parallel to the longitudinal axis in response to rotation of the cam drum about the longitudinal axis; and a fourth linear driver including a fourth cam follower disposed in the second cam groove, the fourth linear driver being supported for movement between advanced and retracted positions in relation to the cam drum along an axis parallel to the longitudinal axis in response to rotation of the cam drum about the longitudinal axis; and a locking mechanism positioned adjacent the distal end portion of the casing, the locking mechanism having a release switch and a lock bar operatively associated one another, the locking mechanism having a locked configuration and an unlocked configuration; and a loading unit including a connector releasably secured within the locking mechanism of the adaptor, wherein in the locked configuration the locking mechanism prevents separation of the adaptor and the loading unit.

15. The instrument of claim 14, wherein the handle interface includes a cam drum input shaft operatively associated with the cam drum to rotate the cam drum about the longitudinal axis.

16. The instrument of claim 14, wherein the adaptor includes a distal cover and an articulation assembly disposed substantially within the distal cover, the distal cover disposed over the distal end portion, the articulation assembly including an articulation shaft, an articulation drum, an articulation cam, and an articulation arm, the articulation shaft extending along an axis parallel to the longitudinal axis and being engaged with the articulation drum to effect rotation of the articulation drum when the articulation shaft is rotated, the articulation cam disposed within the articulation drum, the articulation cam and the articulation drum being radially fixed relative to one another, the articulation cam defining a proximal camming surface and the articulation drum defining a distal camming surface, the articulation arm including an articulation cam follower disposed between the proximal and distal camming surfaces such that as the articulation drum and the articulation cam are rotated about the longitudinal axis, the articulation arm longitudinally translates between a first articulated position, a straight position, and a second articulated position.

17. The instrument of claim 16, wherein the locking mechanism includes a lock arm operatively associated with the lock bar and the articulation drum defines an articulation interlock groove, the articulation interlock groove being aligned with the lock arm to receive the lock arm when the articulation assembly is in the straight position, the articulation interlock groove being offset from the lock arm when the articulation assembly is in an articulated position to prevent the locking mechanism from transitioning to the unlocked configuration.

18. The instrument of claim 14, wherein the distal end portion of the casing defines a locking opening and a locking groove and the loading unit includes a guide lug, the locking groove receiving the guide lug to align the loading unit with the adaptor.

19. The instrument of claim 18, wherein the distal end portion of the casing defines a lug lock which is in communication with the locking groove and is radially offset from the locking groove, the loading unit being secured to the adaptor when the guide lug is captured in the lug lock.

20. The instrument of claim 19, wherein the lock bar is disposed within the locking groove, in the locked configuration of the locking mechanism, the lock bar extends past the lug lock to capture the guide lug in the lug lock and in the unlocked configuration of the locking mechanism the lock bar is retracted proximal to the lug lock allowing the guide lug to rotate out of the lug lock.

* * * * *